(12) United States Patent
Freeman et al.

(10) Patent No.: US 10,888,229 B2
(45) Date of Patent: *Jan. 12, 2021

(54) ESTABLISHING SECURE COMMUNICATION AT AN EMERGENCY CARE SCENE

(71) Applicant: ZOLL Medical Corporation, Chelmsford, MA (US)

(72) Inventors: Gary A. Freeman, Waltham, MA (US); Guy R. Johnson, Gloucester, MA (US); Frederick J. Geheb, Danvers, MA (US); Mark Weary, Billerica, MA (US); Timothy F. Stever, Lowell, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,613

(22) Filed: Nov. 15, 2019

(65) Prior Publication Data

US 2020/0084629 A1 Mar. 12, 2020

Related U.S. Application Data

(63) Continuation of application No. 15/464,515, filed on Mar. 21, 2017, now Pat. No. 10,524,123.

(Continued)

(51) Int. Cl.
*H04W 12/06* (2009.01)
*A61N 1/39* (2006.01)
(Continued)

(52) U.S. Cl.
CPC ........ *A61B 5/0077* (2013.01); *A61B 5/02055* (2013.01); *A61B 5/0402* (2013.01);
(Continued)

(58) Field of Classification Search
CPC .... H04W 12/06; H04W 4/90; A61N 1/39044; A61B 5/0077; A61B 5/02055;
(Continued)

(56) References Cited

U.S. PATENT DOCUMENTS 8,494,576 B1 7/2013 Bye et al.
8,542,827 B2 9/2013 Razzell
(Continued)

OTHER PUBLICATIONS

NXP, NFC for embedded applications, Your critical link for the Internet of Things, 2014, 20 pages.

*Primary Examiner* — Lee Nguyen
(74) *Attorney, Agent, or Firm* — Fish & Richardson P.C.

(57) ABSTRACT

Among other things, we describe a system that includes a first medical device for treating a patient at an emergency care scene, the first medical device including a processor and a memory configured to detect a request for a connection between the first medical device and a second medical device for treating the patient at the emergency care scene, the request for connection including an identifier of the second medical device, responsive to receiving the request for connection, enabling a wireless communication channel to be established between the first medical device and the second medical device based on the identifier of the second medical device and an identifier of the first medical device; and enabling transmission and/or exchange of patient data between the first medical device and the second medical device via the wireless communication channel. Such communications with more than two devices may also be possible.

34 Claims, 13 Drawing Sheets

Related U.S. Application Data

(60) Provisional application No. 62/315,553, filed on Mar. 30, 2016.

(51) Int. Cl.

| | | |
|---|---|---|
| *A61B 5/00* | (2006.01) | |
| *H04W 72/04* | (2009.01) | |
| *A61B 5/0205* | (2006.01) | |
| *A61B 5/0402* | (2006.01) | |
| *A61M 16/00* | (2006.01) | |
| *A61N 1/372* | (2006.01) | |
| *H04W 76/10* | (2018.01) | |
| *H04W 4/80* | (2018.01) | |
| *A61M 16/10* | (2006.01) | |
| *H04L 29/06* | (2006.01) | |
| *H04W 4/90* | (2018.01) | |
| *G16H 40/63* | (2018.01) | |
| *H04L 29/08* | (2006.01) | |
| *A61B 5/021* | (2006.01) | |
| *A61B 5/083* | (2006.01) | |
| *A61B 5/11* | (2006.01) | |
| *A61B 5/145* | (2006.01) | |
| *A61B 5/1455* | (2006.01) | |
| *A61B 5/08* | (2006.01) | |
| *H04W 76/50* | (2018.01) | |

(52) U.S. Cl.
CPC ....... *A61B 5/6801* (2013.01); *A61M 16/0048* (2013.01); *A61M 16/0057* (2013.01); *A61M 16/10* (2013.01); *A61N 1/37252* (2013.01); *A61N 1/39044* (2017.08); *G16H 40/63* (2018.01); *H04L 63/0869* (2013.01); *H04W 4/80* (2018.02); *H04W 4/90* (2018.02); *H04W 12/0609* (2019.01); *H04W 72/04* (2013.01); *H04W 76/10* (2018.02); *A61B 5/021* (2013.01); *A61B 5/0816* (2013.01); *A61B 5/0836* (2013.01); *A61B 5/1123* (2013.01); *A61B 5/14532* (2013.01); *A61B 5/14552* (2013.01); *A61B 2560/0252* (2013.01); *A61B 2560/0257* (2013.01); *A61B 2562/0204* (2013.01); *A61B 2562/0219* (2013.01); *A61M 2205/332* (2013.01); *A61M 2205/3303* (2013.01); *A61M 2205/3368* (2013.01); *A61M 2205/3375* (2013.01); *A61M 2205/3569* (2013.01); *A61M 2205/3592* (2013.01); *A61M 2205/505* (2013.01); *A61M 2230/63* (2013.01); *H04L 67/12* (2013.01); *H04W 76/50* (2018.02)

(58) Field of Classification Search
CPC ... A61B 5/0402; A61B 5/4836; A61B 5/6801; A61M 16/0057
USPC ......................................................... 455/41.2
See application file for complete search history.

(56) References Cited

U.S. PATENT DOCUMENTS

| | | |
|---|---|---|
| 9,125,050 B2 | 9/2015 | Taylor et al. |
| 9,154,191 B2 | 10/2015 | Shimshoni |
| 9,737,656 B2 | 8/2017 | Rosinko |
| 10,524,123 B2 * | 12/2019 | Freeman ........... A61M 16/0048 |
| 2009/0146822 A1 | 6/2009 | Hesham |
| 2014/0181535 A1 | 6/2014 | Smith et al. |
| 2015/0111493 A1 | 4/2015 | Berkema et al. |
| 2015/0118966 A1 | 4/2015 | Locker et al. |
| 2015/0304478 A1 | 10/2015 | Kim et al. |

* cited by examiner

ESTABLISHING SECURE COMMUNICATION AT AN EMERGENCY CARE SCENE

CLAIM OF PRIORITY

This application is a continuation of U.S. patent application Ser. No. 15/464,515, filed on Mar. 21, 2017, which claims priority under 35 USC § 119(e) to U.S. Patent Application Ser. No. 62/315,553, filed on Mar. 30, 2016, the entire contents of which are hereby incorporated by reference.

BACKGROUND

Multiple medical devices may be used in medical situations (for example, emergency situations). These devices can be used by different personnel. For example, automated external defibrillators (AEDs) may be used by non-trained medical device personnel such as a first responders. Additionally, emergency medical technicians (EMT) may use different or additional devices in responding to an emergent situation, which may differ from devices used at a hospital. In addition, there may be one or more information display devices such as liquid-crystal display (LCD) panels, portable computing devices such as tablets, mobile communication devices (e.g., iPhone), smart watches (e.g., iPad, Apple Watch provided by Apple, Inc.), or other types wearable computing and display devices, upon which information from the one or more medical devices can be presented.

In one example, the medical situation is sudden cardiac arrest which is a frequent cause of death. One treatment for cardiac arrest is quick and competent chest compressions to keep blood flowing through a patient's heart. Along with chest compressions, a rescuer can ventilate the patient by either exhaling into the patient's mouth or nose or utilizing a device that pushes air into the patient's lungs. Rescuers, such as lay responders, emergency medical technicians (EMTs), paramedics, doctors, or other rescuers, can benefit from feedback about performance of cardiopulmonary resuscitation (CPR) and from information about the patient's medical status during treatment of the patient. Information about the patient's health status, physiologic data and information about treatment delivered to the patient can be collected by sensors.

SUMMARY

Secure, dynamically reconfigurable networks in accordance with the present disclosure may be accomplished via a four step process: 1) the spatial localization and confirmation, and sometimes also temporal localization and confirmation, of the two or more devices to be configured in a communication network; 2) establishing a secure and/or encrypted close proximity wireless communication channel, e.g., of less than 100 cm (e.g., less than 50 cm, less than about 15 cm, less than about 10 cm, less than about 5 cm) spacing, between the two or more devices such that the communication is highly robust to "sniffing" or other security breach by unwanted third parties; 3) the interchange of one or more secure and/or encrypted identifiers between the two or more devices, and resultant device identity authentication; and 4) the generation of a second secure and/or encrypted intermediate proximity wireless communications channel that has a wider-field (higher power), greater than 15-20 cm, and which uses the secure and/or encrypted identifier or other information from the first established close proximity wireless communications channel to make the second channel secure and/or encrypted, without exposing either channel to data intrusions by unwanted third parties.

For instance, spatial localization (and/or temporal localization) may be determined between devices through a close proximity wireless communications channel based on appropriate criteria for sensed features of the immediate environment. Based on the spatial localization, and sensed feature(s) that determine the spatial localization, mutual authentication and a secure (e.g., encrypted) communications channel may be established between the devices. Authentication of secure communication channels between devices may be one-way (e.g., when pulling data from a device in only one direction) or two-way (e.g., bi-directional communication). Once the secure channel is established, the devices may move away from one another, transitioning to data exchange via an intermediate proximity wireless communications channel, yet still maintaining the mutual or one-way authentication and secure communications channel, based on the original spatial localization and sensed feature(s). Upon detection of a request for disconnection via another sensed feature (which may be according to the same or different criteria for determining spatial localization), the devices may exit out of the secure communications channel. Hence, the network may be secure and dynamically reconfigurable.

In an illustrative embodiment, a system for establishing secure dynamically reconfigurable wireless communications between medical devices, for diagnosing or delivering therapy to a patient, is provided. The system may include a plurality of medical devices. Each medical device may include a receiver and transmitter configured to establish a close proximity wireless communication channel (e.g., using any suitable protocol, such as Bluetooth Low Energy, Near Field Communication, ZigBee, amongst others), for example, having a range of less than 100 cm, with another medical device. The medical device(s) may include a sensor configured to measure at least one feature from an immediate environment of the medical device. The medical device(s) may include another receiver and transmitter configured to establish an intermediate proximity wireless communication channel (e.g., using any suitable protocol, such as Bluetooth, Wi-Fi, ZigBee, ISM radio band, amongst others), for example, having a range of greater than 20 cm, in some cases, up to 100 m, 1 km, or greater. The medical device(s) may include a processor with memory configured to detect a request for connection based at least in part on the at least one sensed feature of the immediate environment, determine whether spatial localization is achieved (e.g., including distance less than 100 cm, less than 20 cm, less than 10 cm, less than 5 cm, etc.) between each device relative to one another based at least in part on the sensed feature of the immediate environment, provide mutual or one-way authentication between each device based at least in part on the spatial localization, and establish a secure communication channel between each device for exchanging patient data including one or more of (i) treatment data indicative of treatment provided to the patient and (ii) patient information.

In another illustrative embodiment, a medical device for establishing secure dynamically reconfigurable wireless communications with a second medical device, for diagnosing or delivering therapy to a patient. The medical device may include a receiver and transmitter configured to establish a close proximity wireless communication channel having a range of less than 100 cm with the second medical device, a sensor configured to measure at least one feature from an immediate environment, and a processor having a memory. The processor with memory may be configured to detect a request for connection based at least in part on the at least one sensed feature of the immediate environment, determine whether spatial localization is achieved relative to the second medical device based at least in part on the sensed feature of the immediate environment, provide mutual or one-way authentication with the second medical device based at least in part on the spatial localization, and establish a secure wireless communication channel with the second medical device for exchanging patient data including one or more of (i) treatment data indicative of treatment provided to the patient and (ii) patient information.

The medical device(s) may be configured to deliver a defibrillation therapy or another resuscitative or medical related therapy. For example, the medical device(s) may be a defibrillator, ventilator, patient monitor, diagnostic apparatus and/or other device used for medical/treatment purposes. The medical device(s) may be wearable, for example, a wearable defibrillator (e.g., LifeVest wearable defibrillator provided by ZOLL Medical Corporation) and/or a wearable patient monitor. In some embodiments, the medical device is a mobile computing device (e.g., phone, tablet, digital assistant).

In some examples, the sensor is the receiver for establishing the close proximity wireless communication channel. For example, the sensor may be configured to measure a field strength of electromagnetic energy for estimating a degree of proximity between devices, or may be configured to sense the presence of another device using a Near Field Communications protocol. The sensor may also be one or more of a camera, motion sensor (e.g., accelerometer), acoustic sensor, or other component for sensing features of the immediate environment. The feature(s) of the immediate environment may be measured by the sensor and may include at least one of an image, a sound, a movement, a code, gestural motion, contact between devices, acceleration, velocity, temperature, amongst other features.

In various embodiments, determination of whether the spatial localization is achieved may be based on whether a threshold is met by the sensed feature. Such a threshold may involve any appropriate measured value (e.g., distance between devices, sound, acceleration, velocity, pressure, power level, etc.). The spatial localization may be based on a correlation between sensed features of each medical device. The correlation between sensed features of each medical device may include correlation between any of a number of features. For example, the correlation may involve motion measured by a first device and a pressure measured by a second device, a motion measured by a first device and a sound measured by a second device, a motion measured by a first device and a motion measured by a second device, a pressure measured by a first device and a sound measured by a second device, a visual image measured by a first device and a motion measured by a second device, a visual image measured by a first device and a display provided by a second medical device, a sound measured by a first device and a sound measured by a second device, or other suitable correlations.

The mutual authentication between devices may involve an identifier (e.g., pre-shared key, code, etc.) that may be shared between devices. The mutual authentication between devices may be based on a spatial localization and/or a temporal localization between devices relative to one another, each involving a sensed feature of the immediate environment. The mutual authentication may occur prior to establishment of a secure wireless communication channel between devices. In some implementations, an identifier from a first device may be employed for authentication with a second device.

The secure communication channel between devices may be established based at least in part on the sensed feature for determining the spatial localization. The secure communication channel may be established based on a correlation between sensed features of each medical device. The secure communication channel may involve use of encryption between each device. The secure communication channel may involve use of proximate tokens between each device. The proximate tokens or sensed feature for determining spatial localization may be mutually known by each device without requiring transmission to the other device. The proximate tokens may be used in a secure key-exchange protocol, such as a Diffie-Hellman protocol. The proximate tokens may include random values input into the secure key-exchange protocol. The proximate tokens may be based on occurrence of an event related to the sensed feature. The occurrence of the event may include at least one of a time of the occurrence, an elapsed time from the occurrence, a contact pressure, a time of release from contact, a velocity of release from contact, a velocity of sensed motion, a shape of a path of a gestural motion, a velocity of movement of an object in an image.

Spatial localization may be achieved between a plurality of devices, for providing mutual or one-way authentication and establishing a secure communication channel between each device. For example, mutual authentication and a secure communication channel may be established between two devices based on the sensed feature(s) for determining spatial localization. One or both of the devices may further sense one or more features for determining spatial localization with a third (or additional) device. The additional device(s) may be further authenticated and enter into the secure communications channel with the existing device(s). In some implementations, the third device may be employed as a mediator for authentication between first and second devices. As an example, a secure identifier or key may be exchanged between a first device and a second device via the accepted spatial localization, and then the second device may achieve an accepted spatial localization with a third device, resulting in a completed mutual or one-way authentication between the first device and the third device, allowing for secure exchange of medical information there between. In such instances, once the authentication and secure communications channel between the first and third devices is established, the second device may also be able to establish a secure communications channel with the first and/or third device, or may be able to be removed from the secure communications network with the first and third devices.

At any point, one or more devices having been authenticated and part of the secure communication channel may exit from the secure network. For example, a request for disconnection may be detected based on one or more sensed features of the immediate environment. In some embodiments, the sensed feature(s) for signaling a request for disconnection may be the same or similar to the sensed feature(s) for signaling the initial request for connection. Alternatively, the sensed feature(s) for signaling a request for disconnection may differ from the sensed feature(s) for signaling the request for connection.

Treatment data may include one or more of data indicative of a shock delivered to the patient, a rate of chest compressions delivered to the patient, a depth of chest compressions delivered to the patient, a duration of compressions delivered to the patient, a rate of ventilation flow to the patient, a volume of ventilation flow to the patient, medication administered to the patient, and/or any other appropriate data indicative of treatment. Patient information may include patient identification data, such as patient history, patient location, patient medical records, etc. Patient information may include patient physiological data. Patient information may include environmental information, such as ambient temperature, air pressure, motion information, video information, audio information, amongst other data indicative of the rescue environment. Patient information may include one or more of an electrocardiogram (ECG) signal of the patient, a blood pressure of the patient, end tidal carbon dioxide of the patient, pulse oximetry of the patient, a temperature of the patient, a respiration rate of the patient, a blood oxygen level of the patient, a pulmonary function of the patient, a blood glucose level of the patient, and/or any other appropriate patient information.

In some embodiments, we describe a system that includes a first medical device for treating a patient at an emergency care scene, the first medical device including a processor and a memory configured to detect a request for a connection between the first medical device and a second medical device for treating the patient at the emergency care scene, the request for connection including an identifier of the second medical device, responsive to receiving the request for connection, enabling a wireless communication channel to be established between the first medical device and the second medical device based on the identifier of the second medical device and an identifier of the first medical device; and enabling exchange of patient data between the first medical device and the second medical device via the wireless communication channel, the patient data including one or more of (i) treatment data indicative of treatment provided to the patient while using one or more of the first medical device and the second medical device and (ii) patient information.

In an aspect, a system for establishing secure dynamically reconfigurable wireless communications between medical devices, for diagnosing or delivering therapy to a patient, includes a plurality of medical devices. Each medical device has a receiver and transmitter configured to establish a close proximity wireless communication channel having a range of less than 100 cm with another medical device; a sensor configured to measure at least one feature from an immediate environment of the medical device; and a processor having a memory. The processor and memory are configured to detect a request for connection based at least in part on the at least one sensed feature of the immediate environment, determine whether spatial localization is achieved between each device relative to one another based at least in part on the sensed feature of the immediate environment, provide mutual authentication between each device based at least in part on the spatial localization, and establish a secure communication channel between each device for exchanging patient data including one or more of (i) treatment data indicative of treatment provided to the patient and (ii) patient information.

Embodiments can include one or more of the following features.

At least one of the medical devices is configured to deliver a defibrillation therapy.

The close proximity wireless communication channel employs a protocol including at least one of Bluetooth Low Energy, Near Field Communication and ZigBee, or similar technology.

The spatial localization includes a distance of less than 100 cm.

The spatial localization includes a distance of less than 20 cm.

The system includes a second receiver and transmitter configured to establish an intermediate proximity wireless communication channel having a range of greater than 20 cm. The second receiver and transmitter are configured to establish an intermediate proximity wireless communication channel having a range of between 20 cm and 100 m. The second receiver and transmitter are configured to maintain the secure wireless communication channel between each device. The intermediate proximity wireless communication channel employs a protocol including at least one of Bluetooth, Wi-Fi, ISM radio band, and ZigBee, or similar technology.

Each device includes an identifier that allows for the mutual authentication between each device, or one-way authentication from a first device to a second device.

The mutual or one-way authentication between each device is based at least in part on a temporal localization between each device relative to one another.

Determination of whether the spatial localization is achieved is based on whether a threshold is met by the sensed feature. The threshold includes at least one of a sensed distance, sound, acceleration, velocity, pressure and power level.

The secure communication channel is established based at least in part on the sensed feature for determining the spatial localization.

The secure communication channel is established based on a correlation between sensed features of each medical device. The secure communication channel involves use of encryption between each device. The secure communication channel involves use of proximate tokens between each device. The proximate tokens or sensed feature for determining spatial localization is mutually known by each device without requiring transmission to the other device. The proximate tokens are used in a secure key-exchange protocol. The secure key-exchange protocol is a Diffie-Hellman protocol. The proximate tokens include random values input into the secure key-exchange protocol. The proximate tokens are based on occurrence of an event related to the sensed feature. The occurrence of the event includes at least one of a time of the occurrence, an elapsed time from the occurrence, a contact pressure, a time of release from contact, a velocity of release from contact, a velocity of sensed motion, a shape of a path of a gestural motion, a velocity of movement of an object in an image.

The mutual or one-way authentication occurs prior to establishment of the secure wireless communication channel.

The receiver is the sensor. The sensor is configured to measure a field strength of electromagnetic energy for estimating a degree of proximity between devices.

The sensor includes at least one of a camera, a motion sensor and an acoustic sensor.

The feature of the immediate environment measured by the sensor includes at least one of an image, a sound, a movement, a code, gestural motion, contact between devices, acceleration and velocity.

The spatial localization is based on a correlation between sensed features of each medical device. The correlation between sensed features of each medical device includes a correlation between at least one of a motion measured by a first device and a pressure measured by a second device, a motion measured by a first device and a sound measured by a second device, a motion measured by a first device and a motion measured by a second device, a pressure measured by a first device and a sound measured by a second device, a visual image measured by a first device and a motion measured by a second device, a visual image measured by a first device and a display provided by a second medical device, and a sound measured by a first device and a sound measured by a second device.

The processor is configured to detect a request for disconnection based on the at least one sensed feature.

The processor is configured to detect a request for disconnection based on a different sensed feature.

The processor is configured to determine whether spatial localization is achieved between a plurality of devices, for providing mutual or one-way authentication and establishing a secure communication channel between each device.

The treatment data includes one or more of data indicative of a shock delivered to the patient, a rate of chest compressions delivered to the patient, a depth of chest compressions delivered to the patient, a duration of compressions delivered to the patient, a rate of ventilation flow to the patient, medication administered to the patient, and a volume of ventilation flow to the patient.

The patient information includes patient identification data.

The patient information includes patient physiological data. The patient information includes one or more of an electrocardiogram (ECG) signal of the patient, a blood pressure of the patient, end tidal carbon dioxide of the patient, pulse oximetry of the patient, a temperature of the patient, a respiration rate of the patient, a blood oxygen level of the patient, a pulmonary function of the patient, and a blood glucose level of the patient.

At least one of the medical devices is a mobile computing device.

At least one of the medical devices is at least one of a defibrillator, a ventilator and a patient monitor. At least one of the medical devices is at least one of a wearable defibrillator and a wearable monitor.

In an aspect, a medical device for establishing secure dynamically reconfigurable wireless communications with a second medical device, for diagnosing or delivering therapy to a patient, includes a receiver and transmitter configured to establish a close proximity wireless communication channel having a range of less than 100 cm with the second medical device; a sensor configured to measure at least one feature from an immediate environment; and a processor having a memory. The processor is configured to detect a request for connection based at least in part on the at least one sensed feature of the immediate environment, determine whether spatial localization is achieved relative to the second medical device based at least in part on the sensed feature of the immediate environment, provide mutual or one-way authentication with the second medical device based at least in part on the spatial localization, and establish a secure wireless communication channel with the second medical device for exchanging patient data including one or more of (i) treatment data indicative of treatment provided to the patient and (ii) patient information.

Embodiments can include one or more of the following features.

The device is configured to deliver a defibrillation therapy.

The close proximity wireless communication channel employs a protocol including at least one of Bluetooth Low Energy, Near Field Communication and ZigBee, or similar technology.

The spatial localization includes a distance of less than 100 cm.

The spatial localization includes a distance of less than 20 cm.

The device includes a second receiver and transmitter configured to establish an intermediate proximity wireless communication channel having a range of greater than 20 cm. The second receiver and transmitter are configured to establish an intermediate proximity wireless communication channel having a range of between 20 cm and 100 m. The second receiver and transmitter are configured to maintain the secure wireless communication channel with the second medical device. The intermediate proximity wireless communication channel employs a protocol including at least one of Bluetooth, Wi-Fi and ZigBee, or similar technology.

Each device includes an identifier that allows for the mutual or one-way authentication with the second medical device.

The mutual or one-way authentication with the second medical device is based at least in part on a temporal localization relative to the second medical device.

Determination of whether the spatial localization is achieved is based on whether a threshold is met by the sensed feature. The threshold includes at least one of a sensed distance, sound, acceleration, velocity, pressure and power level.

The secure communication channel is established based at least in part on the sensed feature for determining the spatial localization.

The secure communication channel is established based on a correlation between sensed features with the second medical device. The secure communication channel involves use of encryption with the second medical device. The secure communication channel involves use of proximate tokens with the second medical device. The proximate tokens or sensed feature for determining spatial localization is mutually known with the second medical device without requiring transmission to the second medical device. The proximate tokens are used in a secure key-exchange protocol. The secure key-exchange protocol is a Diffie-Hellman protocol. The proximate tokens include random values input into the secure key-exchange protocol. The proximate tokens are based on occurrence of an event related to the sensed feature. The occurrence of the event includes at least one of a time of the occurrence, an elapsed time from the occurrence, a contact pressure, a time of release from contact, a velocity of release from contact, a velocity of sensed motion, a shape of a path of a gestural motion, a velocity of movement of an object in an image.

The mutual or one-way authentication occurs prior to establishment of the secure wireless communication channel.

The receiver is the sensor. The sensor is configured to measure a field strength of electromagnetic energy for estimating a degree of proximity with the second medical device.

The sensor includes at least one of a camera, a motion sensor and an acoustic sensor.

The feature of the immediate environment measured by the sensor includes at least one of an image, a sound, a movement, a code, gestural motion, contact between devices, acceleration and velocity.

The spatial localization is based on a correlation between sensed features of with the second medical device. The correlation between sensed features with the second medical device includes a correlation between at least one of a motion measured by the sensor and a pressure measured by the second device, a motion measured by the sensor and a sound measured by the second device, a motion measured by the sensor and a motion measured by the second device, a pressure measured by the sensor and a sound measured by the second device, a visual image measured by the sensor and a motion measured by the second device, a visual image measured by the sensor and a display provided by the second medical device, and a sound measured by the sensor and a sound measured by the second device.

The processor is configured to detect a request for disconnection based on the at least one sensed feature.

The processor is configured to detect a request for disconnection based on a different sensed feature.

The processor is configured to determine whether spatial localization is achieved with the second medical device, for providing mutual or one-way authentication and establishing a secure communication channel with the second medical device.

The treatment data includes one or more of data indicative of a shock delivered to the patient, a rate of chest compressions delivered to the patient, a depth of chest compressions delivered to the patient, a duration of compressions delivered to the patient, a rate of ventilation flow to the patient, medication administered to the patient, and a volume of ventilation flow to the patient.

The patient information includes patient identification data.

The patient information includes patient physiological data. The patient information includes one or more of an electrocardiogram (ECG) signal of the patient, a blood pressure of the patient, end tidal carbon dioxide of the patient, pulse oximetry of the patient, a temperature of the patient, a respiration rate of the patient, a blood oxygen level of the patient, a pulmonary function of the patient, and a blood glucose level of the patient.

In an embodiment, the device includes a mobile computing device.

The device includes at least one of a defibrillator, a ventilator and a patient monitor. The device includes at least one of a wearable defibrillator and a wearable monitor.

In an aspect, a system includes a first medical device for treating a patient at an emergency care scene, the first medical device including a processor and a memory configured to detect a request for a connection between the first medical device and a second medical device for treating the patient at the emergency care scene, the request for connection including an identifier of the second medical device; responsive to receiving the request for connection, enabling a secure wireless communication channel to be established between the first medical device and the second medical device based on the identifier of the second medical device and an identifier of the first medical device; and enabling exchange of patient data between the first medical device and the second medical device via the wireless communication channel, the patient data including one or more of (i) treatment data indicative of treatment provided to the patient while using one or more of the first medical device and the second medical device and (ii) patient information.

Embodiments may include one or more of the following features.

Detecting a request for connection includes detecting an acceleration of the first medical device. The first medical device includes an accelerometer configured to detect the acceleration of the first medical device. The processor and memory are configured to perform an authentication process, including determining that the acceleration of the first medical device occurred substantially concurrently with an acceleration of the second medical device.

Detecting a request for connection includes detecting an audio signal. The processor and memory are configured to perform an authentication process, including determining that the audio signal was detected substantially concurrently with an acceleration of the second medical device.

Detecting a request for connection includes acquiring an image of at least a portion of the second medical device. Acquiring an image of at least a portion of the second medical device includes acquiring an image of the identifier of the second medical device.

Detecting a request for connection associated with a second medical device includes detecting the request for connection through near field communications (NFC), or another protocol for short range communications.

Detecting a request for connection includes detecting a pattern of motion of the second medical device. The pattern of motion of the second medical device is indicative of the identifier of the second medical device. The pattern of motion of the second medical device defines one or more vectors, the one or more vectors being representative of the identifier of the second medical device. The processor and memory are configured to determine a type of wireless communication channel based on the pattern of motion of the second medical device.

Detecting a request for connection associated with a second medical device includes detecting contact between a rescuer holding the second medical device and a predefined region of the first medical device.

Detecting a request for connection includes detecting a gestural motion by at least one of the first medical device and the second medical device.

Detecting a request for connection includes bringing the first medical device and the second medical device within 4 centimeters of one another.

Detecting a request for a connection includes, responsive to detecting an interaction between the first medical device and the second medical device, activating an input device of the first medical device to acquire input associated with the second medical device, the input including the identifier of the second medical device.

The processor and memory are configured to perform an authentication process.

The wireless communication channel includes a secure communication channel.

The wireless communication channel includes a mesh network.

Enabling exchange of patient data includes determining the patient data to be exchanged based on a proximity of the second medical device to the first medical device.

The treatment data include one or more of data indicative of a shock delivered to the patient by the first medical device, a rate of chest compressions delivered to the patient, a depth of chest compressions delivered to the patient, a duration of compressions delivered to the patient, a rate of ventilation flow to the patient, medication administered to the patient, and a volume of ventilation flow to the patient.

The patient information includes health data indicative of a health status of the patient.

The patient information includes one or more of an electrocardiogram (ECG) signal of the patient, a blood pressure of the patient, end tidal carbon dioxide of the patient, pulse oximetry of the patient, a temperature of the patient, a respiration rate of the patient, a blood oxygen level of the patient, a pulmonary function of the patient, and a blood glucose level of the patient.

The first medical device includes a mobile computing device.

The first medical device includes at least one of a defibrillator, a ventilator and a patient monitor.

The second medical device includes a mobile computing device.

The processor and memory are configured to detect a request for a connection between the first medical device and a third medical device for treating the patient at the emergency care scene; and enabling the third medical device to access the secure wireless communication channel.

The processor and memory are configured to detect a request for disconnection between the first medical device and the second medical device, the request for disconnection including data representing a disconnection identifier of at least one of the first medical device and the second medical device.

In an aspect, a system includes a defibrillation device for treating a patient at an emergency care scene, the defibrillation device including a processor and a memory, the processor and memory configured to: detect a signal indicative of contact between a mobile computing device and the defibrillation device; receive an identifier of a mobile computing device through near field communications (NFC) between the defibrillation device and the mobile computing device; enable a secure wireless communication channel to be established between the defibrillation device and the mobile computing device based on the identifier of the mobile computing device and an identifier of the defibrillation device; perform an authentication process, including determining that the signal was detected substantially concurrently with an acceleration of the mobile computing device; and enable exchange of patient data between the mobile computing device and the defibrillation device, the patient data including one or more of (i) treatment data indicative of treatment provided to the patient using one or more of the mobile computing device and the defibrillation device and (ii) health data indicative of a health status of the patient.

The establishment of a secure, dynamically reconfigurable wireless communication channel among devices at an emergency care scene enables information about the health status of a patient or information about the treatment of the patient to be shared among multiple devices involved in the care of the patient. This information can enable care of the patient to be coordinated among the multiple devices and among operators of those devices in a secure, dynamically reconfigurable communications network. Such a secure network may be reconfigurable in a simple manner (e.g., automatically, manually) such that devices may seamlessly join or leave the secure network, triggered by simple actions or proximity based detection (e.g., user actuation, NFC activation, radio frequency, proximity detection, etc.). The medical device(s) may be provided as part of a single integrated apparatus (e.g., circuits within a housing performing various tasks involving sensing, communications, data transfer, processing, analysis, etc.), as separate apparatuses having various medical-related functions, and/or combinations thereof. That is, multiple apparatuses each with one or more processing circuits associated therewith may form a secure dynamically reconfigurable network where, upon entering the network, using processes described herein, each of the processing circuits may be substantially synchronized with one another.

A wireless communication channel can be established through a simple action or can be activated merely by being in relatively close proximity, such that it can be completed quickly by a rescuer, thus enabling the rescuer to maintain focus on providing treatment to the patient. The establishment of a wireless communication channel responsive to a request from a device helps to ensure that patient data remain confidential and that data for a particular patient is exchanged only with devices involved in the treatment of that patient. The configuration and availability of devices can be dynamic and highly reconfigurable. Communication among these devices and the sharing of medical data and information may benefit efficient and proper care of a victim in an emergent situation, as well as drive responder actions and protocol.

Other features and advantages are apparent from the following description and from the claims.

DETAILED DESCRIPTION

Figure 1:
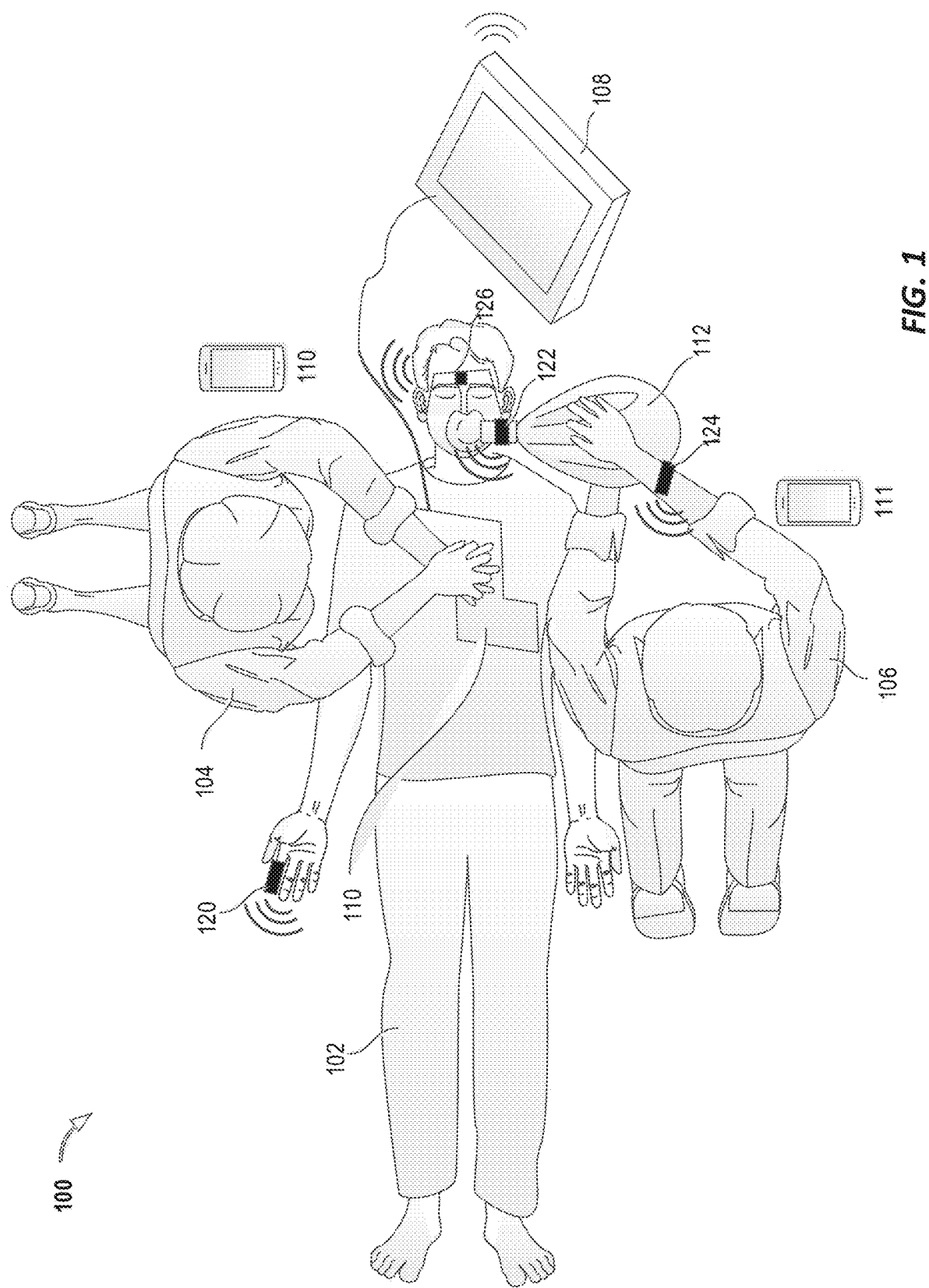
FIG. 1 is a diagram of an emergency care scene.

We describe here an approach to enabling the creation of a secure wireless communication channel among devices, such as defibrillators, mobile devices, or other types of devices, at an emergency care scene. A secure wireless communication channel can be established between devices responsive to a proximity-based interaction between the devices. The secure wireless communication channel enables devices involved in the care of a patient to exchange information about the health status of the patient, information about treatment delivered to the patient, patient physiological information, and/or more. The devices or rescuers using the devices can make use of the secure, exchanged information to efficiently and accurately provide treatment to the patient. When appropriate, such a secure connection may be optionally maintained beyond the emergency care scene, for example, including transport, hospital admission and post-discharge). A number of example use situations are provided below to illustrate the applicability of various embodiments described herein, which allow for devices used in a medical environment to quickly and easily enter and exit the secure dynamically reconfigurable network.

In some situations, a cardiac arrest victim may be wearing a wearable defibrillator such as the LifeVest (ZOLL Medical, Pittsburgh) that continuously monitors the patient's physiologic status and automatically shocks the patient should the device detect that the patient is in cardiac arrest.

In this situation, the device will treat the patient even before the first responders or EMTs arrive. It may be advantageous for either the lay rescuers or EMTs to obtain data from the wearable defibrillator in a way that does not delay further therapies. Accordingly, in an example, it may be advantageous for later responders to be able to hold an appropriate device in close proximity to the wearable defibrillator in a manner that allows the devices to sense features of the environment (e.g., physical tap of the device to the wearable defibrillator, mutual image, motion, pressure and/or sound recognition of each device, etc.) sufficient to determine that a spatial localization has occurred there between. Mutual or one-way authentication and a secure communications channel may be established from the qualified spatial localization, and the devices can then exchange appropriate information. In instances where one-way secure communication channels are established, the direction of data transmission may be limited to one direction from one device to another. For example, a one-way communications channel may be established between a defibrillator/monitor and a central computing device (e.g., central command computer, tablet, mobile device) where medical information (e.g., physiological information, sensed data, historical records, patient data, etc.) may be sent from the defibrillator/monitor to the central computer.

In some situations, the patient may be first treated by lay responders with an AED, and then subsequently after some number of minutes, by more highly trained EMTs, paramedics or doctors who arrive with a more advanced monitor/defibrillator device. It may be advantageous for the advanced rescuers arriving after the start of resuscitation by the lay rescuer to be able to obtain the health status or physiologic or other data immediately upon arrival without having to interrupt the care being provided or delay the transfer of care. Any delays that result from complicated wireless communication setup and configuration may increase the risk of complications and mortality. This data transfer may occur "invisibly" to the rescuers—e.g., in a simple, immediate and transparent fashion, without need for passwords, setting up networks, cables or pressing a sequence of buttons. Hence, according to embodiments described herein, the more advanced rescuers may be able to conveniently and efficiently establish a mutually authenticated, secure communications channel by simply bringing devices sufficiently close to one another so that they are mutually recognizable, for secure data exchange to subsequently occur. Or, at least, a first device may be identified and recognized by a second device for one-way or two-way communications there between. The more highly trained medical personnel may then have quick access to the health status, physiologic data and/or other relevant information.

In another example, the EMTs are arriving at the hospital emergency department (ED), having stabilized the patient at the scene and monitored the patient during transport to the hospital. The ED care providers may require immediate access to the records of treatment and patient data—both status as well as physiologic data. By employing aspects of the present disclosure, the ED care providers may easily access this data quickly and securely.

When a pre-hospital Emergency Medical Services (EMS) team arrives at the hospital emergency department with a patient, the EMS team has already recorded a variety of physiologic data from the monitors and defibrillators at the patient's home or in the ambulance, diagnosed the patient using this information, and then provided one or more therapeutic interventions based on the diagnosis. Currently, all this information is typically communicated verbally or with a short, written run-report to the Emergency Department (ED) staff by the EMS team upon arrival. It can be appreciated that the accuracy of events as well as details may be lost in the verbal or written recounting, and review of the physiologic waveforms themselves by the ED staff for reassessment of diagnostic decisions will be impossible. It is desirable for there to be a simple way for the ED staff to be able to gather data in a concise, efficient fashion from the patient-associated EMS medical devices, at the patient's side, as the patient is being triaged. The data contained in the first patient-associated device—in this case an EMS patient-associated device—can be downloaded to the second patient-associated device—in this case the ED medical devices. The medical devices in either case may be monitors, defibrillators, other treatment devices (e.g., chest compressions devices, ventilation devices, etc.) used for diagnosing and/or treating patients, or may be portable computing devices, which may include mobile computing devices such as phones, computing tablets (e.g., iPad provided by Apple, Inc., Galaxy Tab by Samsung, etc.) and/or other personal computing devices, wearable computing devices such as smart glasses (e.g., Google Glass provided by Google, Inc., amongst others) or smart watches (e.g., Apple Watch provided by Apple, Inc., or others). These portable computing devices may contain information on the patient's medical record or be devices for aiding the triaging and medical intake of the patient. Such devices may be used for managing rescue activities, particularly when several patients are involved. According to embodiments described herein, such devices may be enabled to securely exchange the desired patient data.

In a related use-case scenario, a cardiac arrest victim is being treated by a first responder with an Automated External Defibrillator (AED), which may be recording patient information (e.g., physiological data, ECG, treatment information) or other data relevant to the rescue. These are the types of devices that may be found in one's home or office or public event venue. They will start treating the patient within a few minutes of the cardiac arrest, hopefully, while the EMS system (911) is called and an ambulance is dispatched. It will typically take 5-10 minutes for an ambulance to arrive, during which time the patient will be treated by the first responder using the AED Upon arrival, the Basic Life Support (BLS) or Advanced Life Support (ALS) EMS team, who typically have more medical training than the first responder and are able to deliver more advanced interventions like drugs, etc., rely on the verbal description of the first responder about what has occurred. In this case, the first medical device would be the AED or other portable computing device the lay rescuer has on which they are entering information, and the second medical device is the monitor, defibrillator or portable computing device of the member of the EMS team. The devices may be configured such that the ALS device (e.g., monitor, defibrillator, portable computing device) may establish a secure connection with the first medical device (e.g., AED) and/or other devices (e.g., ventilator, decision support module, etc.) by simply bringing the device(s) into close proximity for them to sense one or more features that allow for a spatial localization between the devices to be determined, which then enables mutual or one-way authentication and secure communications. As a result, the ALS device may be able to download all information related to the rescue for subsequent consideration in diagnosing and/or treating the patient.

In another example, during treatment of a cardiac arrest at a hospital, there is typically a "Code Team" of some sort that is assigned for each work shift to be the primary responders during a cardiac arrest. The Code Team, however, will most often have other medical job responsibilities at the hospital, so when a "Code" is called, the team members will often be arriving from various locations at the hospital at different times, depending on how far they are from the location of the cardiac arrest. In addition, one member of the Code Team will often be responsible for bringing the so-called "Crash Cart," which holds the defibrillator, drugs, and other necessary items for resuscitation. Upon arrival at the patient's room, the Code Team members may desire immediate access to treatment records and patient data, or may desire other information to be exchanged.

Each of the situations presented can make use of dynamically reconfigurable networks.

This desire for immediate, "invisible," dynamically reconfigurable networks can be complicated by two main issues:

First, if more than one medical device is present with wireless communication capability, such as in any emergency department, mass casualty, military or even with a wireless device in an adjacent room in the hospital, it is desirable that the caregiver know for certain that the patient information received is from the patient from whom the caregiver thinks it is, e.g., from the patient next to him and not from a different patient, such as a patient hooked up to a wireless medical device in the next room.

The second significant issue is cybersecurity: Doctor's offices, hospitals, and other healthcare organizations deal with sensitive patient information on a daily basis. This sensitive patient information may include, for example, information descriptive of treatment a patient has undergone, physiologic status and physiologic waveforms, and the patient's past, present, and predicted future health. Given the importance and private nature of sensitive patient information, healthcare organizations implement a variety of security measures to both share and protect it. Cybersecurity measures restrict access to digitized sensitive patient information and equipment dealing therewith. Cybersecurity measures include encrypting sensitive patient information and requiring entry and verification of authentication credentials prior to granting a user access to a computer system or network in which sensitive patient information is stored. The cybersecurity measures employed by healthcare organizations may meet the requirements of any of a variety of information security standards. Examples of these standards include, for example, ISO/IEC 15408 as defined the International Organization for Standardization (ISO), standards defined by regulations promulgated under the Health Insurance Portability and Accountability Act of 1996 (HIPAA), and standards defined by regulations promulgated under the Federal Information Security Management Act of 2002 (FISMA). For instance, FISMA provides the legal basis for certain federal government facilities, such as Veteran's Administration hospitals, to require that equipment processing sensitive patient data be compliant with the Federal Information Processing Standard (FIPS).

It turns out that such levels of appropriate security may contradict some implementations of dynamically reconfigurable networks. It would be desirable and advantageous to have a system whereby a wireless communication in a medical environment could be both secure as well as dynamically reconfigurable with little or no time or effort—"invisible"—on the part of the caregivers using the medical devices.

Hence, it can be readily appreciated that if the process of establishing the secure wireless connection between the first and second medical device is not simple and near-instantaneous, the medical personnel will not perform the process. Such is the case with current 802.11 wireless communication, which may involve the establishment of a local area network with addresses, digital certificates, etc.

Unfortunately, EMS crews arrive to multiple hospitals, each with its own highly secure networks containing patient data and simple, easy fast connections of data are generally not possible between EMS teams and the hospital data networks or data transfer to hospital medical devices. Additionally, even if an EMS medical device has been preapproved for connection into a hospital network or connection to local area networks located in the emergency departments of hospitals, there may be multiple devices within wireless range of the EMS medical device, and it is difficult to know which of the wireless channels is the correct one to be linking with.

It can be appreciated that, at the scene of a mass casualty or mass rescue event involving multiple different patients each with their respective patient-associated medical devices, being triaged, transported and treated, it would be beneficial for the communication networks of medical devices to be quickly reconfigurable in a highly secure fashion, and able to seamlessly move in and out of a wireless secure network without requiring substantial user action. Hence, wireless communication channels between medical devices located in a spatially localized proximity may be secure, patient identity-accurate and dynamically reconfigurable.

The secure, patient identity-accurate and dynamically reconfigurable wireless communication channel is established based on an identifier of the first device and an identifier of the second device. For instance, the wireless communication channel can be established by a handshake process that dynamically sets parameters of the communication channel.

This secure, dynamically reconfigurable network may be accomplished via a four step process: 1) the spatial localization and confirmation, and, at times, also temporal localization and confirmation, of the two or more devices to be configured in a communication network; 2) establishing a secure and/or encrypted close proximity wireless communication channel, for example, of less than about 100 cm (or e.g., less than 80 cm, less than 50 cm, less than 30 cm, less than 15 cm, less than 10 cm, less than 5 cm) spacing between the two or more devices such that the communication is highly robust to "sniffing" by unwanted third parties; 3) the interchange of one or more secure and/or encrypted identifiers between the two or more devices, and resultant device identity authentication; and 4) the generation of a second secure and/or encrypted wireless communications that has an intermediate proximity (wider than the close proximity), for example, greater than 15-20 cm (e.g., or greater than 5 cm, greater than 10 cm, greater than 30 cm, greater than 50 cm, greater than 80 cm, up to 100 m, 1 km, or greater) or otherwise greater in radius than the initial close proximity wireless communications channel, and which uses the secure and/or encrypted identifier or other information from the first established close proximity wireless communications channel to make the second channel secure and/or encrypted without exposing either channel to "sniffing" by unwanted third parties.

That is, rather than requiring a user to potentially spend significant amounts of time in manually configuring the system of each device in the network, or accessing a screen to view and then select from possible device connections, devices located at the emergency scene may be pre-configured to dynamically join and/or leave the secure network or pairing, for example, automatically and/or with one or more simple actions (e.g., switch actuation, pressing a button, near field communication connection, radio frequency, location/proximity recognition, gestural code, tap/bump recognition, motion-activated, sound/vibration, voice command/recognition, amongst others) and/or merely by being in close physical proximity to one another.

Once such wireless connection is made, despite the presence of numerous other devices located nearby, patient information (e.g., physiological data, patient history, rescue info) is able to be sent back and forth between the connected devices in a reliable and secure manner (e.g., according to HIPAA standards, 802.11i protocols) using any suitable type of communication. Rescue devices that are correctly paired can help avoid risk of erroneous patient information to be transmitted between medical devices, which could be detrimental to patient outcomes. In some embodiments, to maintain accurate and secure communications, the proximity-based interaction may invoke an authentication protocol, such as the use of encrypted keys, vector initialization, hash encryption, digital certificates, etc., ensuring no drops and/or leakage of data transfer between devices.

Referring to FIG. 1, at an emergency care scene 100, a rescuer 104 performs cardiopulmonary resuscitation (CPR) on a victim or patient 102 (the terms are used interchangeably here to indicate a person who is the subject of intended or actual CPR and related treatment, or other medical treatment), such as an individual who has apparently undergone sudden cardiac arrest. The emergency care scene 100 can be, for instance, at the scene of an accident or health emergency, in an ambulance, in an emergency room or hospital, or another type of emergency situation. The rescuer 104 can be, for instance, a civilian responder with limited or no training in lifesaving techniques; a first responder, such as an emergency medical technician (EMT), police officer, or firefighter; or a medical professional, such as a physician or nurse. The rescuer 104 may be acting alone or may be acting with assistance from one or more other rescuers, such as a partner EMT 106. In the example of FIG. 1, the rescuer 104 is delivering chest compressions to the patient 102 and the rescuer 106 is delivering ventilations to the patient using a ventilator 112.

In this illustration, the rescuers 104,106 can deploy a defibrillator 108, such as an automated external defibrillator (AED), a professional defibrillator, or another type of defibrillating apparatus, to treat the patient 102. The defibrillator 108 is connected to electrode pads 110 intended to be placed on the patient's chest via one or more cables. The defibrillator 108 provides defibrillation to the patient 102 as appropriate through the electrode pads 110. In some examples, the defibrillator 108 can instruct one or more of the rescuers 104 in providing CPR or other treatment to the patient 102.

The rescuers 104, 106 can use mobile devices 111, such as smartphones, tablets, or wearable devices (e.g., watches or glasses) to assist in treating the patient 102. For instance, a mobile device can provide prompting to assist a rescuer in delivering CPR, ventilations, mouth-to-mouth resuscitation, defibrillation, or other treatments to the patient 102. A supervisor can use a mobile device to coordinate treatment provided by the multiple rescuers 104. Computing devices, such as laptop computers or computing devices integrated into an ambulance, can be used to analyze health data about the patient or data indicative of treatment delivered to the patient or to communicate such data to a remote location (e.g., a dispatch center, an emergency room, or a remote server).

One or more sensors (e.g., sensors 120, 122, 126 in the example of FIG. 1) can be used to monitor the patient 102. For instance, the sensors 120, 122, 126 monitor parameters indicative of the patient's health status, e.g., physical parameters such as the patient's heart rate, electrocardiogram (ECG), blood pressure, temperature, respiration rate, blood oxygen level, end-tidal carbon dioxide level, pulmonary function, blood glucose level, or other parameters indicative of the patient's health status. Some sensors, such as heart rate or ECG sensors, can be included in pads 110 of the defibrillator 108. One or more sensors (e.g., a sensor 124 in the example of FIG. 1) monitor the treatment delivered to the patient 102. For instance, the sensor 124 can monitor shocks delivered to the patient 102 by the defibrillator 108; a rate, depth, or duration of compressions delivered to the patient 102; or other parameters indicative of treatment delivered to the patient. Some sensors can monitor both parameters indicative of the patient's health status and parameters indicative of the treatment delivered to the patient. The sensors 120, 122, 124, 126 can provide information about the patient's health status or information about the treatment delivered to the patient to the defibrillator 108, one or more of the mobile devices 110, 111, or other computing devices at the emergency care scene 100 or to remote computing devices.

A local wireless communication channel can be established among two or more of the devices at the emergency care scene to enable data to be securely and accurately shared among the devices. For instance, referring to FIG. 2, health data about the patient, data indicative of treatment delivered to the patient, or other types of data can be exchanged over the wireless communication channel 200. The exchange of data over the wireless communication channel 200 enables treatment by multiple rescuers to be coordinated in an efficient and accurate manner. In some examples, a wireless communication channel is established among only some of the devices involved in treatment of the patient (e.g., between two of the devices). In some examples, a wireless communication channel is established among all of the devices involved in treatment of the patient.

Figure 2:
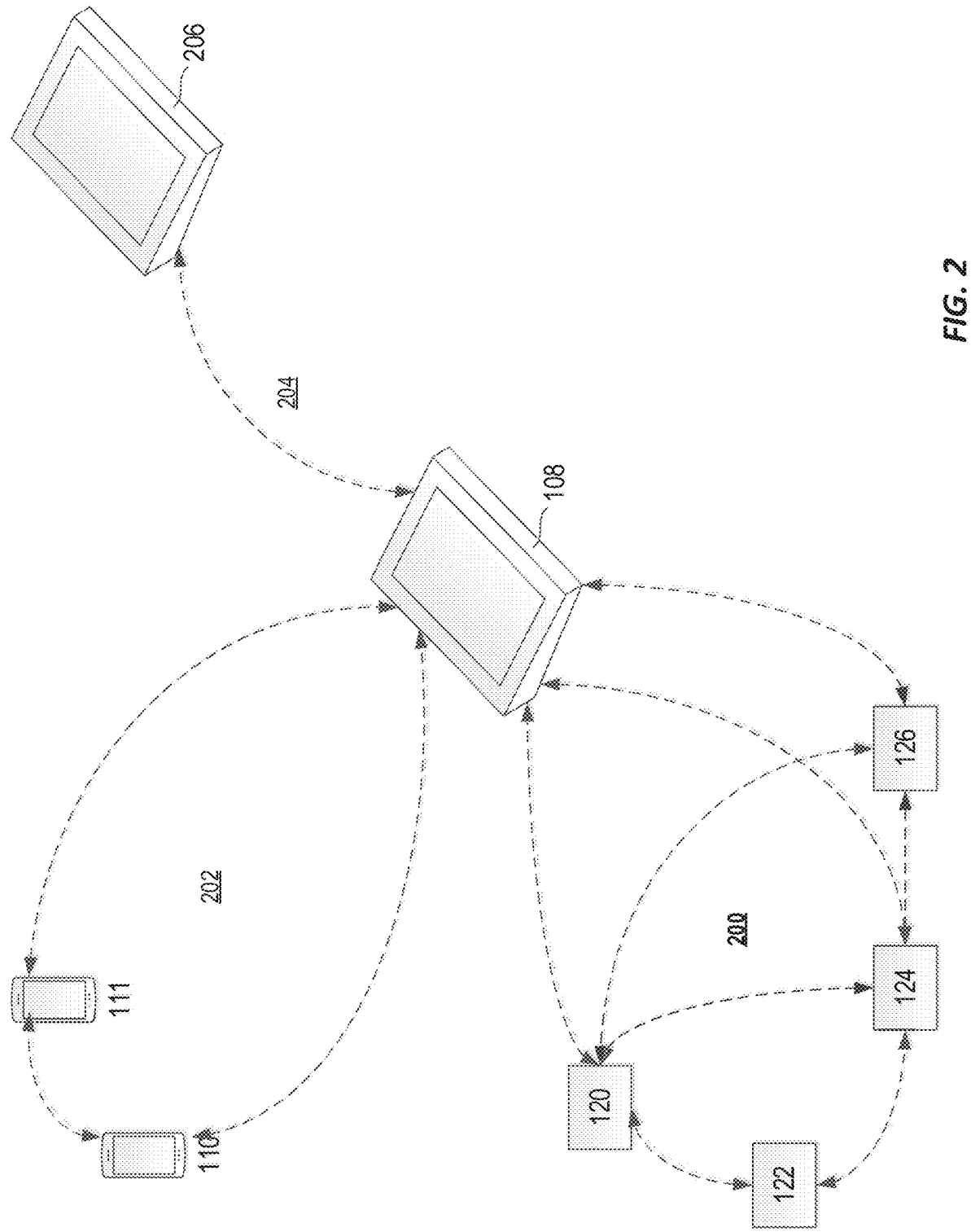
FIG. 2 is a diagram of a communication channel.

Continuing to refer to FIG. 2, in an example, a first wireless communication channel 200 enables communication among the defibrillator 108 and the sensors 120, 122, 124, 126; and a second wireless communication channel 202 enables communication among the defibrillator 108 and the mobile devices 110, 111 involved in treatment of the patient 102. A third wireless communication channel 204 is established between a device being used to treat the patient and a newly arrived device, such as between the defibrillator 108 and a more advanced defibrillator 206 newly arrived at the scene. The three wireless communication channels may be distinct such that, e.g., information exchanged via the first wireless communication channel 200 is not directly communicated to any device that is not connected to the first wireless communication channel. In some examples, communication channels are only established between the defibrillator and any of the sensors 120, 122, 124, 126, e.g., such that none of the sensors have communication channels established among themselves.

In the example of FIG. 2, the communication channels 200, 202, 204 are mesh networks in which each device in the communication channel can communicate directly with each other device, as discussed below. In some examples, the communication channels can be other types of networks, such as networks having a central master device through which all communications pass.

The ability for devices at the emergency care scene to communicate with each other can enable information about the patient's health status or information about treatment delivered to the patient to be shared among the devices. Direct exchange of information among devices can enable information relevant to treating the patient to be displayed on each rescuer's device, thus freeing up rescuers' time and attention to focus on treating the patient. In addition, direct exchange of information among devices can enable the devices to provide more accurate treatment instructions and/or treatment prompting. In an example, exchange of information via a secure wireless communication channel between a rescuer's mobile device and a defibrillator can help achieve efficient and accurate coordination of CPR chest compression prompting with defibrillation. In an example, exchange of information via a secure wireless communication channel between the mobile device of a rescuer delivering CPR chest compressions to a patient and the mobile device of a rescuer delivering ventilations to the patient can help achieve efficient and accurate coordination of CPR chest compressions and ventilations. In an example, exchange of information via a secure wireless communication channel between the mobile device of each of multiple rescuers treating a patient and a supervisor overseeing an emergency care scene can enable the supervisor to easily view information indicative of the health status of the patient and the treatment being delivered by each rescuer, thus enabling the supervisor to efficiently coordinate treatment of the patient.

In some implementations, the communication channel is a secure dynamically reconfigurable communication channel that is capable of automatically incorporating new devices into the channel. For instance, the communication channel can be an ad hoc, self-configuring, self-healing network such as a mesh network. Wireless mesh networks are multi-hop systems in which devices assist each other in transmitting packets through the network. Mesh networks can be implemented with minimal preparation, and can provide a reliable, flexible system that can be extended to many devices, such as sensors or mobile devices involved in patient monitoring or treatment. In a wireless mesh network, multiple nodes cooperate to relay a message to its destination. The mesh topology enhances the reliability of the network. For instance, a mesh network offers multiple redundant communication paths through the network. If one link in the network fails, the network automatically routes messages through an alternate path. In a mesh network, the distance between nodes can be shortened, increasing the quality of the links. A mesh network can be a self-configuring and self-healing network. For instance, a mesh network can determine how to route a message to its destination without control from a system administrator. Adding new nodes or relocating existing nodes can be performed without manual configuration. Rather, the network can discover the new or relocated node and automatically incorporate the node into the existing network.

The wireless communication channel (e.g., the channel 202 in FIG. 2) can be established responsive to a request from a first device (e.g., the mobile device 111) to establish a connection with a second device (e.g., the defibrillator 108). Other devices (e.g., the mobile device 112) can request to join a previously established wireless communication channel. The establishment of a wireless communication channel responsive to a request from a device and the permitting of a device to join a wireless communication channel responsive to a request from the device helps to ensure that devices that are not involved in the treatment of the patient are not enabled to join the wireless communication channel. Patient information can thus be kept confidential among only those devices belonging to the wireless communication channel.

Figure 3:
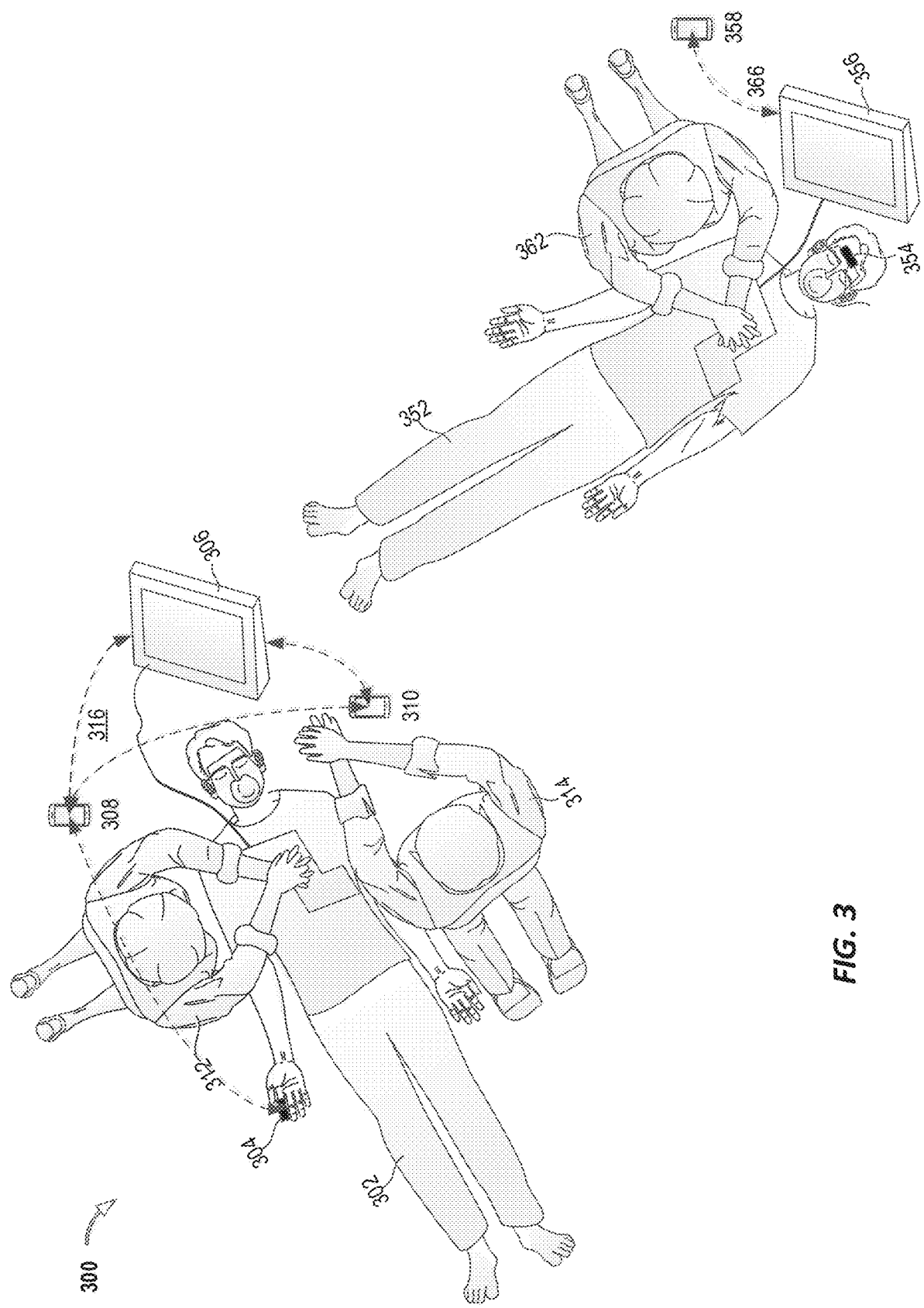
FIG. 3 is a diagram of an emergency care scene.

The establishment of a wireless communication channel responsive to a request from a device to join the wireless communication channel can be useful at an emergency care scene having multiple patients. For instance, referring to FIG. 3, at the scene 300 of a mass casualty or mass rescue event, there can be multiple patients 302, 352. In order to avoid information about one of the patients (e.g., patient 302) from being received by a device treating another one of the patients (e.g., patient 352), a separate communication channel is established for each patient. For instance, a sensor 304 monitoring the patient 302, a defibrillator 306 treating the patient 302, and mobile devices 308, 310 used by rescuers 312, 314 attending to the patient 302 form a communication channel 316. A sensor 354 monitoring the patient 352, a defibrillator 356 treating the patient 352, and a mobile device 358 used by a rescuer 362 attending to the patient 352 form a communication channel 366.

A separate communication channel for each patient in a mass casualty situation helps to ensure that no communication occurs between devices associated with different patients. For instance, in the example of FIG. 3, if the sensor 304 monitoring the patient 302 was able to communicate with the defibrillator 356 treating the patient 352, the information used by the defibrillator 356 to analyze the status of the patient 352 could be compromised. In an extreme example, if the patient 302 regained blood circulation and breathing but the patient's sensor 304 was in communication with the defibrillator 356, the defibrillator 356 could erroneously instruct the rescuer 362 to discontinue administration of CPR on the patient 352. In an extreme example, if a patient's ECG information was transmitted to another patient's defibrillator, the defibrillator could erroneously shock a patient whose heart rhythm was non-shockable. The establishment of a separate, non-overlapping communication channel for each patient can help to avoid such situations. A separate communication channel for each patient in a mass casualty situation can also help ensure confidentiality of patient data, thus preventing a patient's confidential data from being disseminated to an unintended recipient.

Figure 4:
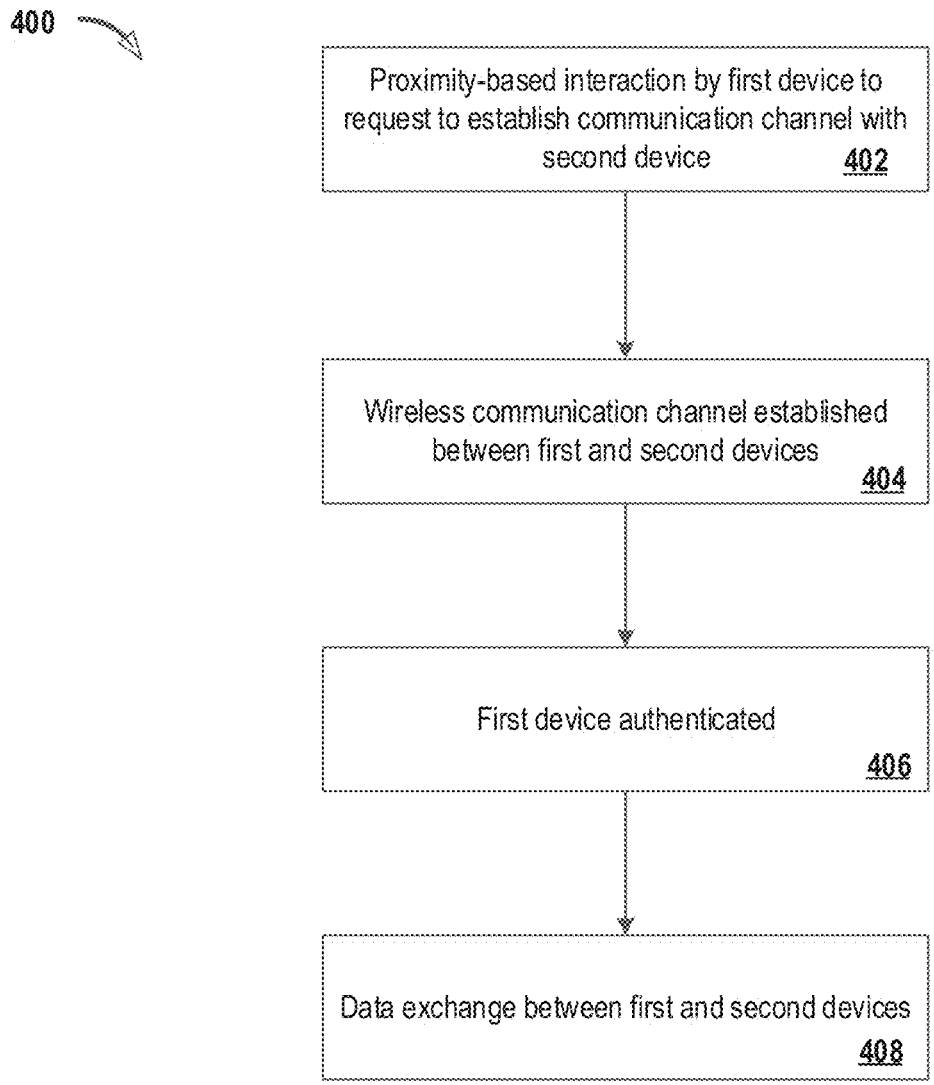
FIG. 4 is a flow chart.

Referring to FIG. 4, a first device can request to establish or join a wireless communication channel with a second device via a proximity-based interaction, which may involve sensing of one or more features of the immediate environment, resulting in the determination of an appropriate spatial localization between devices. The request for connection may include or may be based on an identifier of the first device. The identifier may include a predetermined key or code that indicates to the second device the origin of the first device. Or, the identifier may include data related to the sensed feature(s) that are used for mutual or one-way authentication and/or establishing the secure channel. A proximity-based interaction may include close proximity wireless communication interaction between two closely positioned devices, such as two devices in contact with each other or positioned within a threshold distance (e.g., less than 100 cm, less than 50 cm, less than 20 cm, less than 15 cm, less than 10 cm, less than 5 cm, less than 2 cm, less than 3 cm, less than 4 cm) of each other. Examples of proximity-based interactions, which may result from sensing certain features of the immediate environment (discussed in more detail below), can include, e.g., tapping of the first device against a tap zone on the second device, an acoustic interaction between the first device and the second device, image recognition of the first device or a portion of the first device by the second device, recognition by the second device of a gesture made by the first device, transmission of an electromagnetic (e.g., electronic, radio frequency, etc.) signal from the first device to the second device via a short-range communication protocol (e.g., Near Field communications (NFC), radio frequency identification (RFID), Bluetooth Low Energy, ZigBee, or another short-range communication protocol), or another type of proximity-based interaction. The proximity-based interaction is a simple, efficient interaction that does not take significant time or attention on the part of the rescuers, thus enabling the rescuers to maintain focus on treating the patient. As an example, a caregiver may establish a secure connection via an accepted spatial localization between a mobile device (e.g., smart watch, tablet, smart phone) and a basic life support defibrillator (e.g., public access AED) that is already in use on a patient, and obtain a download of information relevant to the rescue operation (e.g., ECG history, shock history, chest compression history, etc.). The caregiver may then establish a secure connection via an accepted spatial localization between the mobile device and a subsequent, advanced life support defibrillator (e.g., X Series defibrillator/monitor) that arrives on the scene at a later time, allowing the advanced life support defibrillator to obtain all of the information originally received from the basic life support defibrillator. As the patient is transported to the hospital, the caregiver may further establish yet another secure connection via an accepted spatial localization between the mobile device and an advanced life support hospital defibrillator (e.g., R Series defibrillator/monitor), transferring information having been collected by the basic life support defibrillator that was first to arrive on scene and the other advanced life support defibrillator that also arrived on scene. As a result, all relevant rescue information is securely transferred to the appropriate devices for monitoring and treating the patient in an efficient and convenient manner.

A wireless communication channel is established between the first device and the second device, or the first device is enabled to join an existing wireless communication channel to which the second device already belongs.

In some examples, the first device can be authenticated by the second device. Authentication can be performed via a proximity-based interaction, according to one or more sensed features. Authentication of the first device helps to ensure that the device that made the request is the device that is enabled to join the wireless communication channel. Authentication can thus help to prevent unauthorized or unintentional access to a wireless communication channel for a particular patient by other devices not involved in the treatment of that patient (e.g., by devices involved in the treatment of another patient in a mass casualty situation). In some embodiments, prior to authentication, device addresses, associated user codes, and passwords are pre-configured into memory and/or storage of each device so that upon initiation of the proximity-based interaction between pre-configured devices, the authentication protocol for initiating and establishing the secure connection is triggered.

In some examples, both the request by the first device and the authentication of the first device can be performed through a single proximity-based interaction, or by simply bringing the devices within a suitable distance relative to one another. In some examples, the request by the first device and the authentication of the first device are performed by separate proximity-based interactions.

Once the wireless communication channel has been established, patient data can be exchanged between the first and second devices. The patient data can include treatment data indicative of treatment provided to the patient, such as data indicative of a shock delivered to the patient by the first medical device, a rate of compressions delivered to the patient, a depth of compressions delivered to the patient, medication administered to the patient, and a duration of compressions delivered to the patient. The patient data can include health data/parameter(s) indicative of a health status of the patient, such as data indicative of an electrocardiogram (ECG) signal of the patient, a blood pressure of the patient, a temperature of the patient, a respiration rate of the patient, a blood oxygen level of the patient, a pulmonary function of the patient, a blood glucose level of the patient, and/or other appropriate patient-related information.

Figure 5:
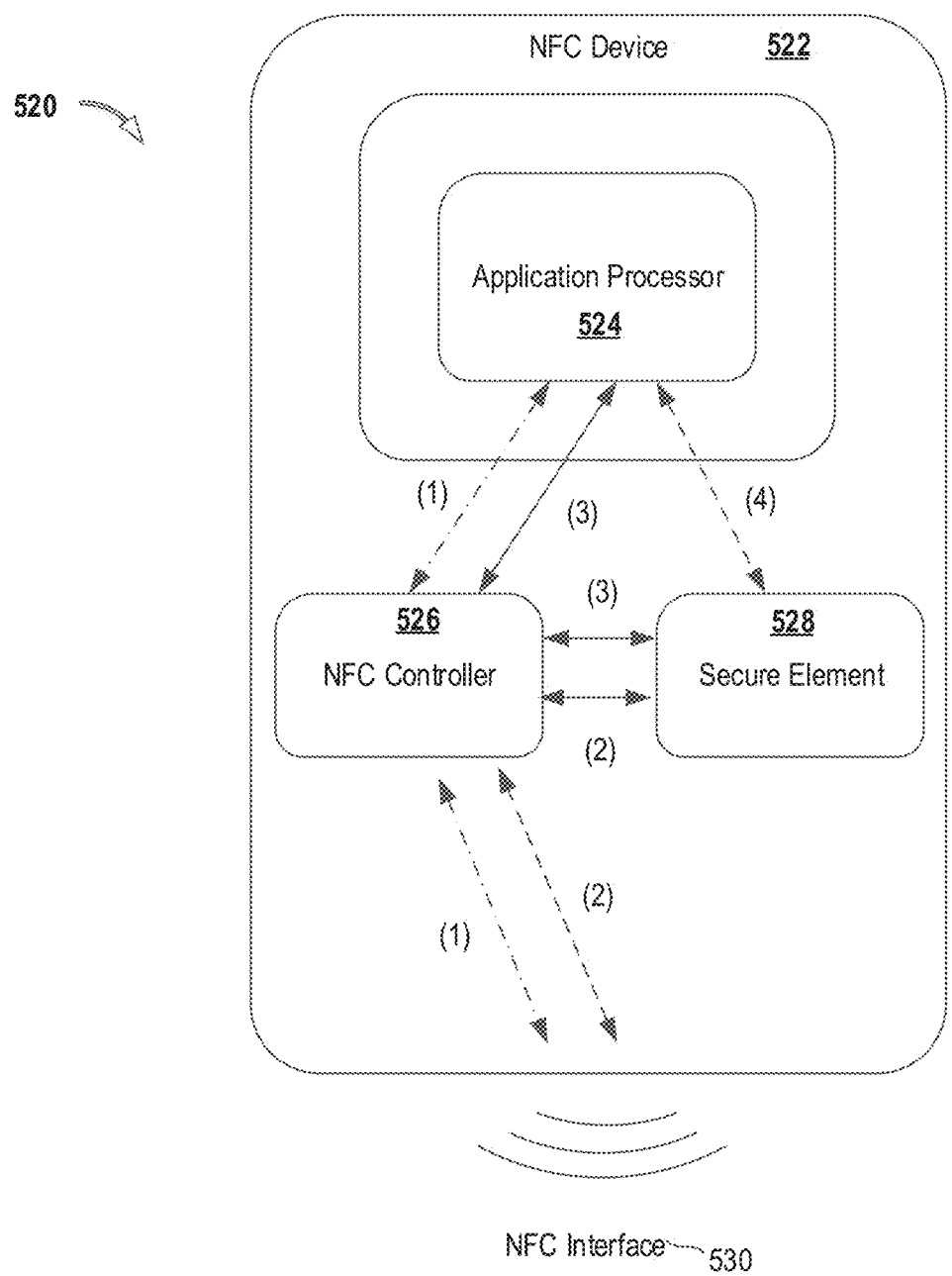
FIG. 5 is a diagram of Near Field communication functionality in a computing device.

FIG. 5, in some embodiments, spatial localization for the close proximity wireless communications channel may be accomplished using a Near Field Communication (NFC) protocol, although it can be appreciated that other communications protocols may be possible. Hence, spatial localization between devices sufficient for authentication and establishing the secure channel may be determined by merely bringing the devices in sufficiently close physical proximity. Though, for some embodiments, other sensed features in addition to the close physical proximity may also be used, such as a suitable level of motion, pressure/force, sound, image detection, etc.

While a close proximity wireless communications channel may employ a NFC protocol, it should be understood that other communications protocols (e.g., Bluetooth Low Energy, ZigBee, amongst others) may be employed for close proximity wireless communications. Near field Communication (NFC) is a set of communication protocols that enable two electronic devices, one of which may be a portable computing device such as a smartphone, to establish communication by bringing them within approximately 4 cm (2 in) of each other. NFC is a set of short-range wireless technologies, typically requiring a separation of 10 cm or less. NFC facilitates the integration of contactless technology into active device platforms, such as mobile phones. NFC is a short-range RFID technology operating at the 13.56 MHz radio frequency (RF) band and is described in the ISO 18092/ECMA 340 and in ISO 21481/ECMA 352 standards. NFC is specified to be compatible with existing contactless systems adhering to ISO 14443, ISO 15693 and FeliCa. The standards specify both 'passive' and 'active' operation. Passive operation corresponds to the operation of conventional contactless systems. The NFC device can therefore either act like a contactless token, interacting with a reader, or act like a reader, powering and interacting with a contactless token. Two NFC devices can also interact with each other in active, or peer-to-peer (P2P) mode, when brought in close proximity. In this active mode, devices take turns to transmit an RF field, e.g. device 1 turns on its RF field and transmits data to device 2, followed by device 1 turning off its field and device 2 turning on its field and transmitting data to device 1.

NFC may use magnetic induction between two loop antennas located within each other's near field, effectively forming an air-core transformer. It operates within the globally available and unlicensed radio frequency ISM band of 13.56 MHz. Most of the RF energy is concentrated in the allowed ±7 kHz bandwidth range, but the full spectral envelope may be as wide as 1.8 MHz when using ASK modulation. Theoretical working distance with compact standard antennas: up to approximately 20 cm (practical working distance of about 10 cm). Supported data rates include: 106, 212 or 424 kbit/s (the bit rate 848 kbit/s is not compliant with the standard ISO/IEC 18092).

In order to implement a more secure NFC, a Trusted Execution Environment (TEE) may be implemented in each of the medical devices, which may also be FIPS compliant. The TEE may be a secure area of a processor of a smart phone or other mobile device that protects the confidentiality and integrity of code and data loaded inside. In some embodiments, the TEE is the same as implemented on many smartphone systems: Trusted Execution Environment (TEE): The TEE is usually realized through the use of a secure element (SE) and provides secure data storage, execution and application management. A SE is essentially a smart card supporting Java Card 2.2.1 (Java Card Open Platform), Global Platform 2.1.1 and selected legacy products such as the Mifare Classic emulation. An SE is most commonly implemented as an embedded module, e.g., a surface-mounted module soldered into the device, as an integrated component on the (U)SIM (Universal/Subscriber Identity Module), or as a removable secure memory token. A recent development is the concept of a "soft-SE" located within the device application area. The "soft-SE" is open for development, in contrast to earlier SE modules that had to be unlocked for development use. For example, using an "unlock" application supplied by the device manufacturer. Once unlocked, an SE is forever considered as untrusted and can subsequently be used only for development purposes. An NFC device will contain one or more of these SE implementations.

Although the range of NFC is typically limited to a few centimeters, NFC alone does not ensure secure communications. Because NFC devices usually include ISO/IEC 14443 protocols, relay attacks may be feasible. For this attack the adversary forwards the request of the reader to the victim and relays its answer to the reader in real time, pretending to be the owner of the victim's smart card. This is similar to a man-in-the-middle attack.

In some embodiments, various methods may be utilized to minimize risk of so-called relay or man-in-the-middle attacks. One such technique is the Distance-bounding protocols which determine an upper bound for the physical distance between two communicating parties based on the Round-Trip-Time (RTT) of cryptographic challenge-response pairs.

FIG. 5 shows the elements of the NFC functionality within the device. 1. The application processor is the device's main processor that hosts the operating system and runs applications. 2. The NFC Interface is the radio interface where signals can be sent and received. 3. The NFC controller is the main component of all NFC related functionality. It controls the radio interface and does preprocessing on the data. 4. The secure element may be a separate integrated circuit (a smart card chip) in the phone that provides secure storage and a secure runtime environment. Secure storage means that information stored on the chip is physically protected and cannot be extracted. A secure execution environment means that the execution of programs on the chip cannot be tampered with. Secure elements are based on smart card technology and are evaluated and certified according to high security standards and therefore they provide good security. The secure element also conforms with the organization described in ISO 7816-4.

In some embodiments, the NFC controller is responsible for all physical communication operations, such as anti-collision, token selection, communication parameter setup and data formatting for transmission. During anti-collision and token selection a unique hardware identification (UID) may be used. The legitimate device and the attacker's proxy-token in theory therefore have different UIDs. If the transaction data is linked to a UID, the verifying recipient observes that the UID in the data does not correspond to the UID of the device it is communicating with, thus detecting the relay.

Specific countermeasures may be employed for a variety of different attack methods, such as: eavesdropping; data corruption where the attacking device attempts to corrupt the data; data modification where the attacking device attempts to modify the data; and data insertion where the attacking device attempts to insert data.

A NFC protocol by itself cannot protect against eavesdropping. In general, data transmitted in a passive mode is significantly harder to be eavesdropped on, but just using the passive mode is likely not sufficient for most applications that transmit sensitive data.

Data Corruption—NFC devices can counter this attack because they can check the RF field, while they are transmitting data. If an NFC device does this, it will be able to detect the attack. The power which is needed to corrupt the data is significantly greater than the power which can be detected by the NFC device. Thus, every such attack can be detectable.

Data Modification—Protection against data modification can be achieved in various ways. NFC devices can check the RF field while sending. This means the sending device could continuously check for such an attack and could stop the data transmission when an attack is detected.

While initial eavesdropping may be a possible threat, when operating the NFC channel particularly in the passive mode, the channel is robust to relay and other man-in-the-middle attacks since the sender of the information will be able to sense when other intermediaries are attempting to intervene in the communication channel.

In some embodiments, a secure channel between two NFC devices may be established to protect against eavesdropping and data modification attacks. A standard key agreement protocol such as Diffie-Hellmann based on RSA or Elliptic Curves, where cryptographic keys are exchanged over a public channel, could be applied to establish a shared secret between two devices. The shared secret can then be used in encryption to derive a symmetric key such as for 3DES or AES, which may then be used for the secure channel providing confidentiality, integrity, and authenticity of the transmitted data. Various modes of operation for encryption methods such as 3DES and AES could be used for such a secure channel and can be found in literature as known to those skilled in the art. Other modes of encryption and/or secure communications may be employed.

Besides the standard key agreement mechanism, it is also possible to implement an NFC specific key agreement. This one does not necessarily require any asymmetric cryptography and therefore reduces the computational requirements significantly. Theoretically, it also provides perfect security.

One such scheme works with 100% ASK only and it is not part of the ISO standard on NFC. The idea is that both devices, say Device A and Device B, send random data at the same time. In a setup phase the two devices synchronize on the exact timing of the bits and also on the amplitudes and phases of the RF signal. This is possible as devices can send and receive at the same time. After that synchronization, A and B are able to send at exactly the same time with exactly the same amplitudes and phases.

While sending random bits of 0 or 1, each device also listens to the RF field. When both devices send a zero, the sum signal is zero and an attacker, who is listening, would know that both devices sent a zero. This does not help. The same thing happens when both, A and B, send a one. The sum is the double RF signal and an attacker knows that both devices sent a one. More interestingly, once A sends a zero and B sends a one, or vice versa, both devices know what the other device has sent, because the devices know what they themselves have sent. However, an attacker only sees the sum RF signal and the attacker cannot figure out which device sent the zero and which device sent the one. For the bit combinations (A sends 0, B sends 1) and (A sends 1, B sends 0) the result for the attacker is absolutely the same and the attacker cannot distinguish these two cases.

The two devices now discard all bits, where both devices sent the same value and collect all bits, where the two devices sent different values. They can either collect the bits sent by A or by B. This arrangement can be agreed on start-up, but it doesn't matter. This way A and B can agree on an arbitrary long shared secret.

In some embodiments, the shared secret for establishing the secure wireless communication channel includes a token containing information that can only be known by the two devices in physical proximity with each other. This token may be termed a "proximate token." For instance, at least one of the devices may include a region of its surface that has a physical proximity sensor (e.g., pressure/force sensor, motion sensor, camera) for sensing features of the immediate environment such as whether and to what degree contact has been made with the surface. Such a region may be termed a "tap zone." In some embodiments, the "tap zone" may encompass the whole device such as in the case of a cellphone or other mobile handheld device where the mobile device has an accelerometer as its physical proximity sensor that can detect when the cellphone is hit against another object via measuring and detecting the deceleration forces. The detection of the "hit" of the whole device against the other device may be enabled by a tap zone.

It can be appreciated that any combination of sensed features may be employed so as to constitute a "hit" in determining spatial localization between devices to be subject to mutually secure data exchange. For example, the "hit" may be based on mutual contact between the devices, as detected from motion and/or force sensors. Alternatively, the "hit" may involve features sensed from a transmitter/receiver (e.g., electromagnetic signal), camera (e.g., moving images, still image(s)) and/or other suitable sensor(s).

Figure 6:
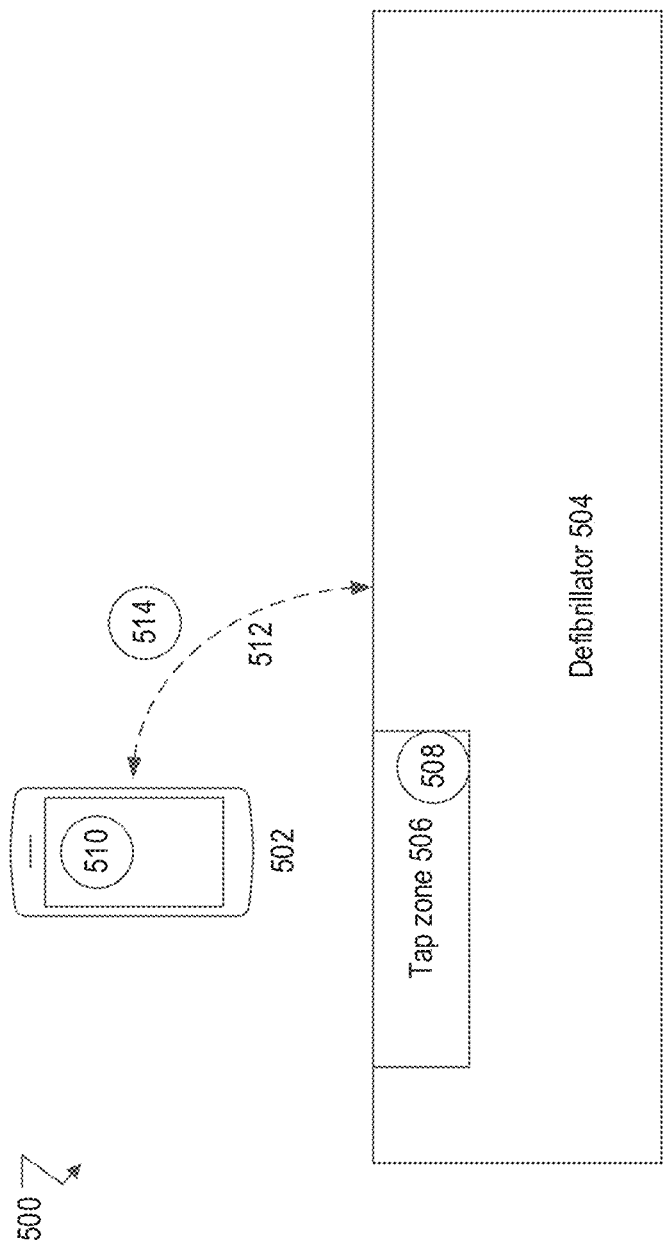
FIG. 6 is a diagram of an approach to establishing a wireless communication channel.

The physical proximity sensors for sensing features of the immediate environment do not necessarily need to be the same on both devices. For instance, on one device the physical proximity sensor may be an accelerometer, such as the Analog Devices ADXL02, and on the second device a pressure sensor such as a simple switch or a pressure sensor, such as a force-sensing resistor (FSR) such as the FSR 406 manufactured by Interlink Electronics (Camarillo Calif.) or a load cell, known to those skilled in the art. FIG. 6 shows a mobile device 502 approaching a tap zone approach 500 to establish a secure wireless communication channel between a first device (in this example, a mobile device 502) and a second device (in this example, a defibrillator 504). In some embodiments, mobile device 502 may contain an accelerometer as a physical proximity sensor and the defibrillator 504 may contain a pressure sensor as a physical proximity sensor that occupies a region on the defibrillator 504 marked as the tap zone. In this example, at the time of hitting the tap zone of the defibrillator 504, the mobile device 502 detects a deceleration in excess of a threshold (e.g. approximately 0.2 g) and determines that a "tap" has occurred and sends out an unencrypted communications initiation request via the NFC channel. The antenna for the NFC radio will, by necessity, be co-located or very close nearby (<12 inches) to the demarcated tap zone on the device.

Determination of physical proximity based spatial localization may be used as part of the communication authentication process. Authentication is the act of verifying a claimed identity, as the originator of a message (message authentication) or as the end-point of a channel (entity authentication). Two roles can be distinguished: the user that is being subject to identification and the authenticator which is the entity that performs authentication. In some embodiments, the authentication is one way, e.g. the defibrillator is authenticating the identity of a mobile device. Alternatively, each device may authenticate the other. This is called mutual authentication. For highest security, mutual authentication is employed. Though, in some cases, as noted herein, one-way authentication may be employed where one device is authenticated to another device.

An authentication protocol is responsible for performing secure authentication over an insecure channel. This can be accomplished by using cryptography and a challenge/response mechanism. The authenticator asks a question (challenge) to the user and if the response is a valid answer (response), the authentication is successful. A commonly used example of a challenge/response is a password. Using a password, however, will not prevent eavesdropping attacks because if the password is sent as plain text over the communication channel it can be intercepted by an attacker. Sending the password encrypted does not solve this problem: although now an attacker cannot read the password it can still replay the conversation between a user and authenticator.

A secure channel provides secure transfer of data, which may be referred to as application data, over an insecure communication channel such that the properties of a secure system, i.e. confidentiality, integrity and availability, are not violated. This may be accomplished in the following way:

1. Authentication is optional. It is done before any application data is sent in order to establish that the communicating party is who it claims to be.

2. The application data is encrypted before it is sent. Typically, symmetric encryption is used because this is computationally less expensive compared to asymmetric encryption.

3. Optionally, a key exchange protocol establishes a secret key that is used for the symmetric encryption. This is referred to as the session key.

4. Message authentication codes (MACs) are added to the data. MACs are designed to detect any intentional or unintentional changes which guards the integrity of the application data. It uses cryptographic algorithms such as encryption (CMAC) or a hash function (HMAC).

Since secure channels and authentication protocols are closely related, most authentication protocols can help with setting up a secure channel. During the authentication, both parties negotiate a set of parameters for the secure channel. These parameters are referred to as the security association. This includes the session key, and encryption algorithms (also referred to as the cipher suite). These parameters are then used to secure all communication that takes place after the authentication.

In some embodiments, authentication may be subdivided into a first portion that authenticates based on physical proximity spatial localization, and then a second portion during which the secure channel is established.

In one embodiment, the first portion of the authentication, the physical proximity (PP) authentication is accomplished via an unsecure, unencrypted "open" channel. For example, referring to FIG. 7, the communications authentication flow diagram shows the time-course of information exchange necessary for the mutual authentication of the example mobile device and the defibrillator, starting from the mobile device "hitting" the defibrillator in its tap zone (labeled "Hit" at the top of the diagram), down to the mutual authentication events at the bottom of the diagram. Lateral arrows show the information elements transmitted from mobile device to defibrillator or vice versa. The text labels at the base of the lateral arrows indicates what information is sent, while the text at the arrowhead side of the arrows is the result on the receiver side of that information. At the time of the Hit, both devices recognize a "Hit" event: for instance, the mobile devices detect when the acceleration or the change in acceleration (sometimes called "jerk" in the literature) exceeds some threshold. The threshold value may be approximately 1.5 g's, or another appropriate value. The threshold for the pressure sensor of the defibrillator tap zone might be approximately 0.5 pounds, or another appropriate value. When a Hit is detected, in one embodiment, the following process may be followed to obtain physical proximity mutual authentication:

1.) Both devices generate random numbers, $RND1_S$ and $RND1_F$, then wait an appropriate amount of time. The time increments may be the same for both devices. If they are different, then the time increment value may be mutually transmitted later on as one of the data exchange elements in the PP authentication process.

Figure 7:
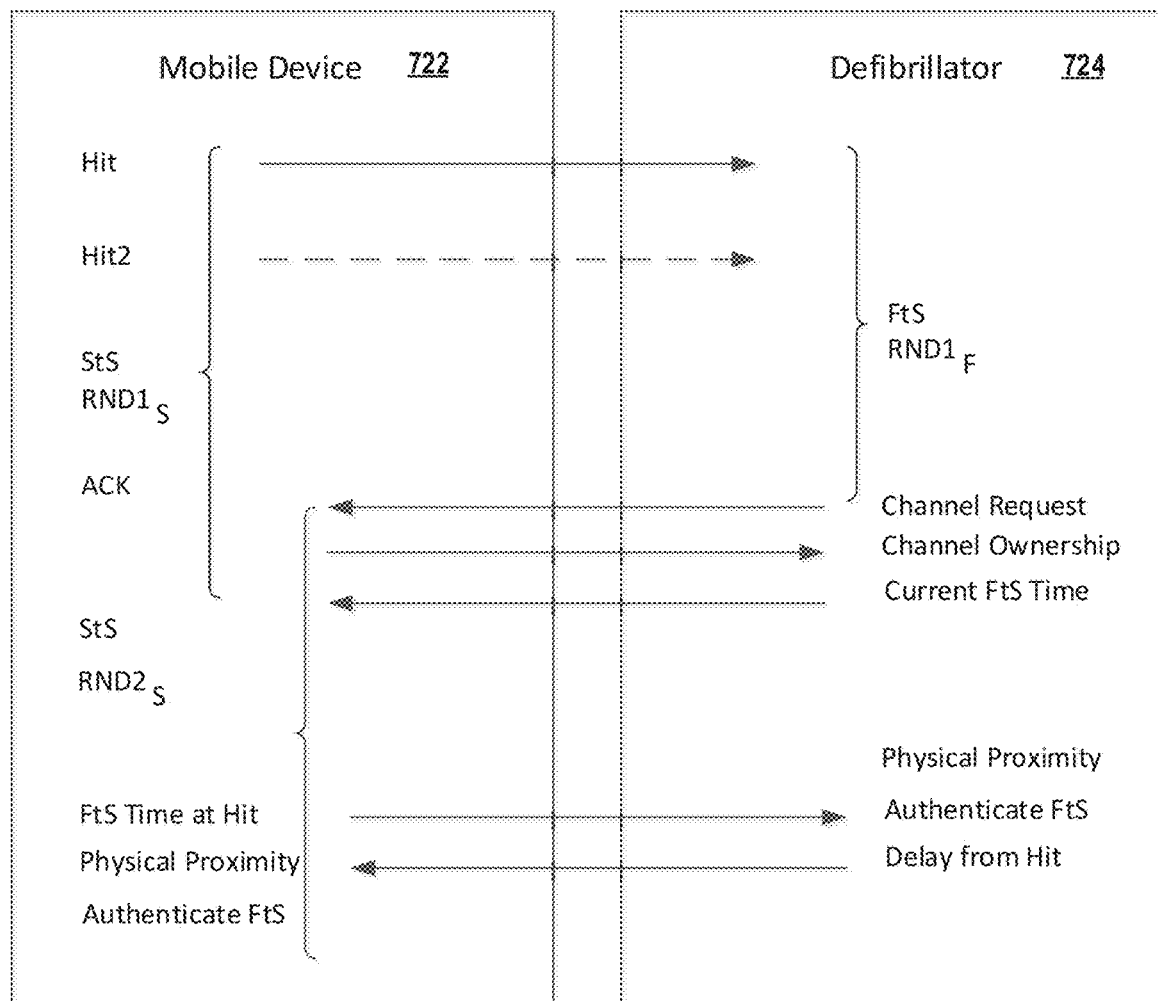
FIG. 7 is a diagram of communications flow for requesting connection and authentication.

2.) As soon as either device has waited the particular random time—$RND1_S$ or $RND1_F$, then that particular device sends a "Request to Connect?" (RtC?) query to the other device. This is shown on FIG. 7 as "Channel Request." The device with the smallest random number, and thus the shortest wait time, we term "First to Send" (FtS), and the device with the larger random number, we term "Second to Send" (StS). The mobile device and the defibrillator each have an equal chance, each time, of being the FtS; "StS" and "FtS" labels in FIG. 7 are just by way of example.

3.) A standard collision detection is performed by the requesting device, and if the channel is clear, FtS takes control of channel.

4.) StS sends acknowledge (ACK) message indicating acceptance. StS stores what its wait time was at the time it received the RtC? message (this is its estimate of $RND1_F$), and generates a second random number $RND2_S$ (in some embodiments, StS re-uses $RND1_S$) and starts a new timer and begins to wait that time.

5.) FtS sends its current time, at time of message send. This allows for StS to calculate the time difference between the FtS and StS clocks.

6.) At end of its wait interval, StS sends its estimate of what it thinks the FtS time was at the time of the Hit. StS can estimate this accurately based on its knowledge of $RND1_S$ and $RND1_F$, and the time difference between StS and FtS clocks.

7.) FtS authenticates StS identity based on physical proximity based a correct estimate by StS of FtS time at Hit. By sending only FtS time at Hit, the random numbers are kept secret.

8.) FtS sends delay from Hit. StS authenticates FtS identity based on physical proximity as a result of FtS' correct estimate of time from Hit. In some embodiments, two or more Hits may be used, and the authentication may be based on FtS sending the time from Hit1 to Hit2. In this way, the random numbers, $RND1_S$ and $RND1_F$, will not have been exposed for "sniffing" by unwanted third parties and can be used singularly, or in combination, as the proximate token for use in creating the session key. In some embodiments, a second Hit may not be needed for creating a secure proximate token. For instance, the use of a second Hit may be replaced by a predetermined second feature of the first Hit that would only be known to the mobile device and the defibrillator (or whatever two devices are being used), e.g. the time of release or the velocity of release.

In some embodiments, various other combinations of sensor pairs may be utilized to authenticate physical proximity spatial localization, using various correlated sensing modalities such as: motion sensed by a first device and pressure sensed by a second device (motion-pressure); motion sensed by a first device and sound sensed by a second device (motion-sound); motion sensed by a first device and motion sensed by a second device (motion-motion); pressure sensed by a first device and sound sensed by a second device (pressure-sound); image sensed by a first device and motion sensed by a second device (image-motion); image sensed by a first device and display sensed by a second device (image-display); sound sensed by a first device and sound sensed by a second device (sound-sound), amongst other combinations, where each feature sensed may be of sufficient intensity to reach a suitable threshold for evaluating whether spatial localization has been achieved.

As an example of motion-sound, an accelerometer and microphone combination may be used, where the pressure sensing element of the defibrillator is replaced by a microphone, and the Hit is when the mobile device is tapped on the defibrillator microphone located within the tap zone.

Alternatively, the motion-motion combination may be embodied in a trackpad on the first device, e.g. a defibrillator, and a motion sensing function in a smart watch, e.g., Apple Watch. With this embodiment, when the finger of the smart watch wearer is moved across the trackpad features of the path of motion will be known to the smart watch as well, e.g. shape of the path such as a circle or "x," maximum or average velocity of the gesture on the trackpad and time of the start and start of the gesture on the trackpad. Any two of these parameters may be chosen in advance for the minimum of two features known only by the two devices for the generation of the proximate token. When one or more time parameters are included, then the process is termed spatiotemporal localization, rather than just spatial localization. For example, the secure dynamic communication(s) may be initiated by a spatial localization of the devices being in close physical proximity, and further at approximately the same time, as a verification that communications are allowed to occur. By performing this security check (e.g., at any point during communication there between), the devices may then be able to exchange data between one another in a secure fashion.

Similarly, an alternative embodiment for the camera-motion combination might be a camera on the defibrillator and accelerometer on the mobile device similar to that of a mobile phone (e.g., iPhone), table (e.g., iPad) or a smart watch (e.g., Apple Watch). In this case, the detection of the deceleration Hit by the mobile device initiates the contact, and then the authentication information known only by the two devices might be a subsequent gesture (e.g. an "x" in space traced by the mobile device) that is measured by the mobile device motion sensor and seen by the defibrillator camera. Any one of the parameters such as in the previous paragraph may be used for authentication, and any two pre-agreed-to parameters such as in the previous example may also be used for the generation of the proximate token.

Another embodiment of the camera-display combination, the camera and display such as on mobile device, for example, an iPhone or iPad where the camera and display face in the same direction. The second device also has such an arrangement of the camera and display. The camera may be just above the display, such as the "selfie" camera (e.g., camera on the same face as the display of the device) on the iPhone and other mobile phones. In this case, the "Tap zone" may be a small region on either or both displays or a printed region, in some embodiments near to one or both of the cameras which cannot be readily discerned from more than 2-12 inches away. That is, the "tap zone" is not necessarily required to be specifically tied to motion or contact and may be related to another feature, for example, an image, sound and/or another aspect of the immediate environment. Rather, the "tap zone" may be a region on a device from which a sensed feature related to such a zone may be used to determine whether a spatial localization has been achieved for establishing secure connections. Referring back to the example, the small region may contain a unique visual code, such as a bar code, 2D bar code and/or QR-code (e.g., displaying on a screen such as a secondary screen, or as a sticker). In order to minimize computational complexity, the tap zone may be positioned on top of, or in close proximity to the two cameras. When either one or both of the devices detects the presence of the unique visual identifier, then it sends out an RtC? query, as described previously. Each device then displays a visual location marker on each display such that each camera can see the other's display location marker. The location markers may be simple, small "x's" on the displays; they may also be the QR codes themselves. The user then moves the first device in front of the camera/tap zone of the second device. When the second device sees or otherwise visually detects the display marker on the first device move to the left, the second device moves the display marker on its display a commensurate amount to the left; when the second device sees or visually detects the display marker on the first device move to the right, the second device moves the display marker on its display a commensurate amount to the right. The same holds true for the first device. In such a fashion, the two display markers will "lock-on" to the locations of the opposite cameras and stop moving laterally relative to the cameras, as the cameras are passed over each other.

In some embodiments, the control system for determining the commensurate amount of lateral motion of the display markers may be a proportional-differential (PD) controller, known to those skilled in the art. Alternatively, the control system may be a proportional-integral-differential (PID) controller. In some embodiments, the two secret shared parameters between the devices may be from among: speed at time of cross-over of cameras, time at time of crossover, etc. Either or both of the devices may also have an accelerometer or other motion sensor or pressure sensor that may be used for the detection of the Hit to initiate the RtC? query and authentication process.

In another embodiment, the sound-sound combination may involve each device having a stereo microphone and at least one sound generating element such as a speaker, piezoelectric sound generator, etc. positioned directly above, or very close to (+/−0.5 inches) the microphone. Similarly, to that of the previous example with the camera-display, the two microphones may be passed over each other in a motion by the user. The sound generating elements can deliver either short pulses or a continuous waveform like a sinusoid outside the audible range (e.g. 20-100 KHz; with pulses 5-50 microseconds in duration delivered at a rate of 100-5000 pulses per second). The two devices may negotiate two separate frequencies, so that both can output sound at the same time. Based on the measured phase information between the stereo microphone pickup, the angular position of the microphones can be determined relative to the other device's sound generator. If the sound generators are located along a vertical line with the microphone, then the measured angular position will be zero (directly over the microphone) at the same time for both devices. The two parameters can then back, for example time at which they pass directly over each other and the speed of angular motion (or change in phase difference over time.)

As discussed, the secure communications channel may be able to seamlessly transition from a close proximity wireless communications channel to an intermediate proximity wireless communications channel, and vice versa. This may be beneficial because the close proximity wireless communications channel is used to determine whether a suitable degree of spatial localization has been achieved, based on sensed features. Authentication and establishing a secure communications channel may then flow from the spatial localization. Though, secure data exchange may still be able to occur once the devices are moved apart from one another, to an intermediate proximity wireless communications channel.

NFC generally supports much lower data rates compared to Wi-Fi, Bluetooth, or other wireless schemes, and more critically, NFC will only support communication distances of approximately one foot or less. Thus, on its own, it may not be useful for communicating large quantities of patient information between various medical devices in for instance an Emergency Department or at the scene of a car accident. The system thus transitions from authentication over a close proximity wireless communications network such as using NFC protocols to an intermediate (wider) proximity wireless communication such as Wi-Fi or Bluetooth. In some embodiments, the final steps of securing the communication via encryption is achieved while the two devices are still communicating via NFC, and before Wi-Fi communications have been established.

This can be accomplished by the secure features of NFC: the international standard NFC-SEC and NFC-SEC-01 provide some security features in NFCIP-1. In various embodiments, this can be used in NFC peer-to-peer mode rather than, for example, in read/write and card emulation mode.

NFC-SEC provides two services:

1. Shared secret service: establish a shared secret key and a symmetric encryption algorithm in a secure way.

2. Secure Channel Service: establish a secure channel by encrypting all data symmetrically using the previously defined shared secret key and chosen encryption algorithm.

The other standards of the form NFC-SEC-xx specify the implementation of these services using specific algorithms (thus cipher suites). Currently, NFC-SEC-01 is available which uses elliptic curve Diffie-Hellman algorithm 2 for establishing the shared secret key and Advanced Encryption Standard (AES) 3 for establishing the secure channel.

Thus, NFC-SEC provides a secure channel which provides protection against eavesdropping and data modification. However, it might not provide sufficient authentication against man-in-the-middle attacks. Accordingly, such man-in-the-middle vulnerability may be addressed with the addition of authentication based on physical proximity and/or other manner of spatial localization.

The proximate token is thus a one-time use authentication and encryption token. In some embodiments, it may be used with Diffie-Hellman or Diffie-Hellman with Elliptic Curves for further authentication and encryption.

Diffie-Hellman (D-H), is a means of keeping "Perfect Forward Secrecy." D-H keeps using the private key for authentication but uses an independent mechanism to agree on a shared secret. There exists a well-known protocol for this: the D-H key exchange. It is a method of exchanging keys without any prior knowledge. Diffie-Hellman may also be achieved with elliptic curves: Diffie-Hellman key exchange with the help of elliptic curve cryptography which is based on the algebraic structure of elliptic curves over finite fields. Elliptic curve cryptography allows one to achieve the same level of security than RSA with smaller keys. For example, a 224 bit elliptic curve is likely to be as secure as a 2048 bit RSA key.

The standard D-H key exchange can be translated to elliptic curves. Instead of defining p and g, you get some elliptic curve, $y2=x3+ax+\beta$, a prime p and a base point G. All those parameters are public. In fact, while they can be generated by the server, this is a difficult operation and they are usually chosen among a set of published ones.

The use of elliptic curves is an extension of TLS described in RFC 4492. Unlike with the classic D-H key exchange, the client and the server agree on the various parameters. A typical D-H algorithm follows the general procedure below:

1. The server picks a random integer a and computes aG, which will be sent, unencrypted but signed with its private key for authentication purpose, in a Server Key Exchange message.

2. The client checks that the signature is correct. It also picks a random integer b, and sends bG in a Client Key Exchange message. It will also compute b☐aG=abG which is the premaster secret from which the master secret is derived.

3. The server will receive bG and compute a☐bG=abG which is the same premaster secret known by the client.

4. An eavesdropper will only see aG and bG and won't be able to compute efficiently abG.

With the proximate token determined based on spatial or spatio-temporal localization and physical proximity authentication, at least two random numbers are generated that are secretly known by both parties and do not necessarily need to be transmitted across the unencrypted communication channel. Thus the eavesdropper will not be able to read "a" or "b," making the channel even more secure.

Embodiments described herein may be used in accordance with systems and methods described in Ser. No. 15/084,249, filed on Mar. 29, 2016, entitled "Clinical Data Handoff in Device Management and Data Sharing" and provided as Appendix A, and Ser. No. 15/084,369, filed on Mar. 29, 2016, entitled "Customer- or Patient-Based Selective Data Encryption in Medical Device Management" and provided as Appendix B, each of which is hereby incorporated by reference in its entirety.

In one embodiment, the local network between the medical devices is dynamically and securely established by first employing so-called network cloaking by the server, e.g., the server suppresses the broadcasting of its Service Set Identifier (SSID). Any additional medical or user devices can then only join when they explicitly request that SSID. Network cloaking does not stop a determined attack on the network and therefore cannot replace other security practices. That unbroadcast, preknown SSID may be as simple as "ZOLLMEDICAL" or may be a more complex, apparently random sequence of alphanumerics that may be generated via an encryption algorithm, using a master key known only to ZOLL Devices further encrypted at the time of the event using a seed that incorporates, for instance, the proximate token.

Additionally, there may be only pre-approved MAC addresses and MAC filtering may be employed. Pre-shared key mode (PSK, also known as Personal mode) may also be employed. Both WPA2-PSK and WPA2-EAP result in a Pairwise Master Key (PMK) known to both the supplicant (client) and the authenticator (AP). (In PSK the PMK is derived directly from the password, whereas in EAP it is a result of the authentication process.) The four-way WPA2 handshake essentially makes the supplicant and authenticator prove to each other that they both know the PMK, and creates the temporal keys used to actually secure network data.

Figure 8:
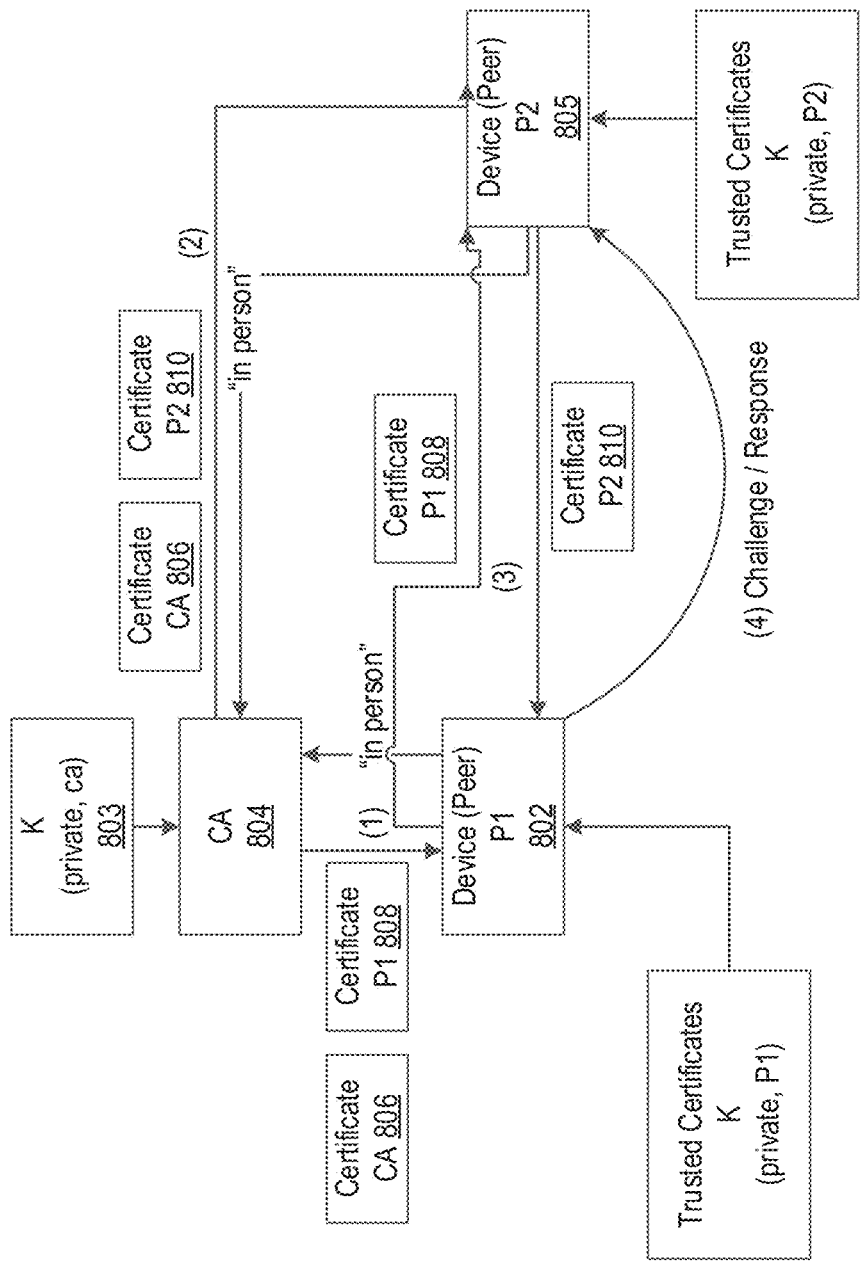
FIG. 8 is a diagram of public-key infrastructure (PKI) authentication architecture.

Alternatively, a Public-key infrastructure (PKI) may be used for establishing a secure channel. In a public-key infrastructure (PKI), certificates are used for the purpose of authentication. A certificate is a virtual document that allows an authenticator to verify the identity of a user without having any prior knowledge about the user (such as a pre-shared key used in PSK), according to one example. Several forms of public-key infrastructures exist. FIG. 8 is one example of a PKI authentication architecture. In the figure, the numbers indicate the order of events. In FIG. 8, a PKI architecture is shown in simple form, in which one extra entity is involved called the certificate authority (CA) 804. The set up process for all peers is to get a certificate at the CA. The CA is responsible for checking the identity one time 'in person'. In the case of a Near Field Communication (NFC) mobile phone for example, the set up process could be done during the manufacturing of the phone/secure element as the "in person" check in. After the CA 804 has verified the identity of a requester, called peer 1 (P1) 802, it creates and signs a certificate $C_{p1}$ 808. A well-known standard for certificates is X.509 defined in RFC 2459. The information 1 on the certificate 808 includes the identity information of the peer (which may be referred to as Ip1) and the CA that signed it (which may be referred to as Ica), a public key (Kpub, p1) and a signature (Sp1).

The signature is calculated by hashing and encrypting $K_{pub, p1}$ and $I_{p1}$ using the CA's private key ($K_{priv, ca}$) 803. After signing, the CA 804 gives the requester its certificate $C_{p1}$ 808. Furthermore, the CA 804 provides its own certificate (Cca) 806 to the requester containing the public key ($K_{pub, ca}$). $C_{ca}$ 806 is a special type of certificate indicating that it can be used to sign other certificates but $C_{CA}$ is not signed itself, according to one example. After this, the set up process is finished, according to one example.

All peers keep a list of CA certificates that are trusted which, in this example, implies that every peer with a certificate signed by one of the CAs in its list is trusted. Therefore, this list may be chosen carefully and protected from unintended change, in such examples. When two peers, p1 802 and p2 805, want to authenticate each other, they first exchange certificates. They each verify that the certificate was signed by a CA that they trust. This is done by decrypting the signature on the peer's certificate with the public key of the CA (which is on the certificate of the CA). Subsequently, the peers each verify that the other owns the private key corresponding to the public key on the certificate. This can be done by a challenge/response mechanism similarly as done in PSK. Private keys remain confidential to their owners, in this example, including the private key of the CA 804. Though in the example discussed here, a PKI with one CA has been described, it is possible to have a hierarchical infrastructure of certificate authorities, in which certificate authorities in tier 2 have a certificate signed by a certificate authority in tier 1, which in turn is signed by the root certificate authority. The root certificate authority may have a self-signed certificate meaning that the signature is calculated from its own private key, in some cases, in which the certificate authorities below the root certificate authority inherit the trustworthiness of the root certificate authority. This architecture is useful in large systems for load balancing. PKI schemes like EAP-TLS, EAP-TTLS, EAP-IKEv2 may be employed, or other schemes known to those skilled in the art, based on the present disclosure.

Capturing the four-way handshake will not divulge the PMK or PSK (since capturing the handshake is trivial over wireless this would be a major vulnerability). The PMK isn't even sent during the handshake, instead it is used to calculate a Message Integrity Check (MIC). The session key is generated using a combination of things, for instance, including the proximate token or other random elements contained with the proximate token.

Other example forms of encryption that may be used in accordance with embodiments described herein are provided in the table below:

Information Processing Standard. Specifically, devices with cryptographic capabilities are currently expected to comply with FIPS 140-2. There are 4 levels of compliance, ranging from use of approved and validated algorithms at level 1 up through full physical/tamper-proof security at level 4.

FIPS 140-2 poses many challenges for medical devices because the standard was not developed with this application in mind, but rather as a general-purpose data-communication standard. It imposes many requirements concerning the transfer of data across the boundaries of the cryptographic module, the software environment in which the cryptography is run, the verification/validation of the cryptographic software, and the management of encryption keys. Because the NFC element is a physically secure chip that can be appropriately housed within the medical device, it is inherently designed to be compatible with FIPS requirements. In one embodiment, a defibrillator is made to be FIPS compliant by using an NFC chip mechanically housed within the defibrillator in a tamper-resistant, tamper evident location.

As noted herein and referring back to FIG. 6, the tap zone on the defibrillator can be configured to detect when an item, such as a mobile device, comes into contact or close proximity with the tap zone. The tap zone can detect

| Encryption Type | Description |
| --- | --- |
| Identity-Based Encryption | Identity-based encryption (IBE) is an encryption process that can be initiated by a sender using a unique identifier such as the recipient's e-mail address in calculate a public key. A trusted third-party server, called the private-key generator, uses a cryptographic algorithm to calculate the corresponding private key from the public key. The benefit of IBE is that senders can easily generate the public key of the recipient. When the recipient needs to acquire their private key, they simply send a request to the private-key generator. The key advantage is that no one has to worry about distributing their public key, allowing anyone to encrypt data and securely send it or sign data to assure authenticity. Encryption techniques have relied on randomly generated keys that are mapped to identities called digital certificates. The management of these certificates and the need to procure a certificate before encrypting a message or record has made encryption using traditional approaches very difficult for end users, costly to operate, and complex for IT operations. IBE can use any arbitrary string as a public key, enabling the PAN or a transaction to be protected without the need for certificates. In a payments scenario, the PAN and discretionary data found on the card are encrypted immediately after the data is acquired using the public key thus negating the need for temper-resistant hardware. IBE supports magnetic stripe and contactless and contact chip cards. IBE uses any number of public key encryption algorithms offering a variety of levels of security. |
| Symmetric Key Encryption | In symmetric key encryption, each computer has a secret key that it can use to encrypt a packet of information before it is sent over the network to another computer. Symmetric key encryption requires that you know which computers will be talking to each other so you can install the key on each one. The key provides the key to decoding the message. With symmetric key encryption as used in payments, the PAN and discretionary data are encrypted when read by tamper-resistant hardware. Symmetric key encryption supports magnetic stripe and contactless and contact chip cards. It uses 128-bit TDES or AES format-preserving symmetric key encryption. |
| Asymmetric Key Encryption | Asymmetric encryption is a form of encryption where keys come in pairs. What one key encrypts, only the other can decrypt. Frequently, but not necessarily, the keys are interchangeable in the sense that if key A encrypts a message then key B can decrypt it, and if key B encrypts a message then key A can decrypt it. While asymmetric key encryption supports magnetic stripe and contactless and contact chip cards, it is typically used for card-not-present transaction encryption when referenced in terms of payment. Asymmetric key encryption is used to encrypt data (e.g., Track 1 and Track 2) as well as the transaction. |

Embodiments described herein may be used in accordance with systems and methods described in a US provisional application, filed on Mar. 30, 2016, entitled "Systems and Methods of Integrating Ambulatory Medical Devices" and provided as Appendix C, which is hereby incorporated by reference in its entirety.

Additional description of the establishment of a wireless communication channel can be found in U.S. Pat. Nos. 9,125,050, 9,154,191, U.S. 2014/0181535, U.S. 2015/0111493, U.S. 2015/0118966, and U.S. Pat. No. 8,494,576, the contents of all of which are incorporated here by reference in their entirety.

Communications-capable devices sold to the federal government are expected to comply with FIPS, the Federal physical proximity by detecting a type of stimulus, such as sound, force, pressure, acceleration, deceleration, or another stimulus.

The mobile device 502 requests to enter into a wireless communication channel with the defibrillator 504 by tapping on a tap zone 506 of the defibrillator 504. By tapping, the user of the mobile device 502 (e.g., a rescuer) may bring the mobile device 502 into brief contact with the tap zone 506 of the defibrillator 504. The defibrillator 504 senses a feature of the environment, indicating the request by detecting the tap of the mobile phone 502 on the tap zone 506. In some examples, the tap zone 506 occupies a portion of the second device (e.g., a portion of the defibrillator 504). In some examples, the entire second device can form the tap zone.

Responsive to the tapping, using any suitable method in accordance with the present disclosure, a wireless communication channel 512 is established between the mobile device 502 and the defibrillator 504, or the mobile device 502 is enabled to access an existing wireless communication channel to which the defibrillator 504 belongs.

In the example of FIG. 6, the defibrillator 504 has an acoustic sensor 508, such as a microphone, that senses the tap of the mobile device 502 by detecting the sound or vibration of the mobile device 502 coming into contact with the tap zone 506. In some examples, a force sensor or a pressure sensor in the tap zone 506 can detect the tap of the mobile device 502 on the tap zone 506 by detecting a force or pressure exerted on the tap zone 506 by the mobile device 502. In some examples, the second device can have a motion sensor, such as an accelerometer, that can sense the tap of the mobile device 502 on the tap zone 506 by detecting an acceleration of the second device, or a portion thereof, induced by the tapping of the first device against the tap zone 506 of the second device. The detection of an acceleration of the second device induced by the tapping of the first device is generally feasible when the first and second devices have similar masses, e.g., when the first and second devices are both mobile devices. Accordingly, when one device taps against another similar sized device, both devices detect slight movement or acceleration, triggering the authentication protocol there between.

In some examples, the tap is inferred, e.g., not physically detected. For example, a transceiver (e.g., a transceiver for a wireless commination technique such as NFC, RFID, or Bluetooth) may sense the presence (and also the intensity level) of a signal associated with the mobile device 502. By sensing the intensity level of a signal, the device(s) may be able to estimate the relative distance from one another. For example, the devices may be in close proximity (e.g., within 3-5 cm), yet not in contact. Though, having been pre-configured to detect an appropriate motion-related (e.g., motion toward one another, yet without making actual contact) or other type of activation, the devices may identify one another and come into mutual or one-way communication. Accordingly, the presence of the signal can be used to infer that the mobile device 502 has been tapped to the tap zone 506.

The request for connection by the first device includes an identifier of the first device. In some examples, the identifier of the first device can be sensed and/or communicated through a specific pattern of taps. For instance, the mobile device 502 can be tapped on the tap zone 506 of the defibrillator 504 with a specific pattern of taps, e.g., three taps in quick succession. The specific pattern of taps may be a sensed feature of the immediate environment representative of the identifier of the mobile device 502. In some examples, the identifier of the mobile device 502 can be transmitted via a close proximity communication protocol, such as NFC, RFID, Bluetooth, or another communication protocol. For example, the identifier, e.g., data representing an identity of the mobile device 502 and/or permission for secure data exchange to occur, can be transmitted by a transceiver of the mobile device 502, and received by a transceiver of the defibrillator 504. As another example, the identifier is stored on a component (e.g., an RFID chip) of the mobile device 502, and a transceiver of the defibrillator 504 reads the stored data from the component (e.g., by activating the RFID chip and retrieving the data from the RFID chip).

In some examples, the pattern of taps can be a sensed feature used to determine spatial localization and to authenticate the mobile device 502. For instance, the detection of a specific pattern of taps indicates that the mobile device 502 is tapping in order to request a connection and reduces the possibility that the taps are a result of inadvertent contact, e.g., by a device that is not requesting connection.

In some examples, authentication of the first device can be performed by comparing the taps detected by the defibrillator 508 and the taps detected by the mobile device 502. For instance, the mobile device 502 has an accelerometer 510 that detects a deceleration of the mobile device 502 when the mobile device 502 taps on the tap zone 506, an acoustic sensor 508 that detects the sound of the mobile device 502 coming into contact with the tap zone 506, or both. In some implementations, once the tap trigger has been sensed and initiated, one or more authentication signals 510 are transmitted between the mobile device 502 and the defibrillator 504, e.g., via an appropriate close proximity wireless communication protocol, such as NFC, RFID, Bluetooth Low Energy, or another communication protocol or via the wireless communication channel during the authentication process for transmission of the authentication signals 514. The authentication signals 514 include information sufficient to authenticate that the mobile device 502 sending or receiving the authentication signals 514 is the same device that tapped on the tap zone 506 of the defibrillator 502. For instance, an authentication signals 514 sent from the mobile device 502 to the defibrillator 504 can include information indicative of the time at which the deceleration of the mobile device 502 was detected, for determining temporal localization between devices. The defibrillator 504 compares information in the authentication signal 514 indicative of the time at which the deceleration of the mobile device 502 was detected with the time at which the sound of the mobile device 502 coming into contact with the tap zone 506 was detected. If the two times match (indicating that the sound was detected substantially concurrently with the acceleration), the mobile device 502 is authenticated as the same device that tapped on the tap zone 506.

In the example of FIG. 6, the authentication signal 514 is sent from the mobile device 502 (the requesting device) to the defibrillator 504. In some examples, the authentication signal 514 can be sent from the defibrillator 504 to the mobile device 502. In some examples, an authentication signal 514 can be sent in both directions.

Figure 9:
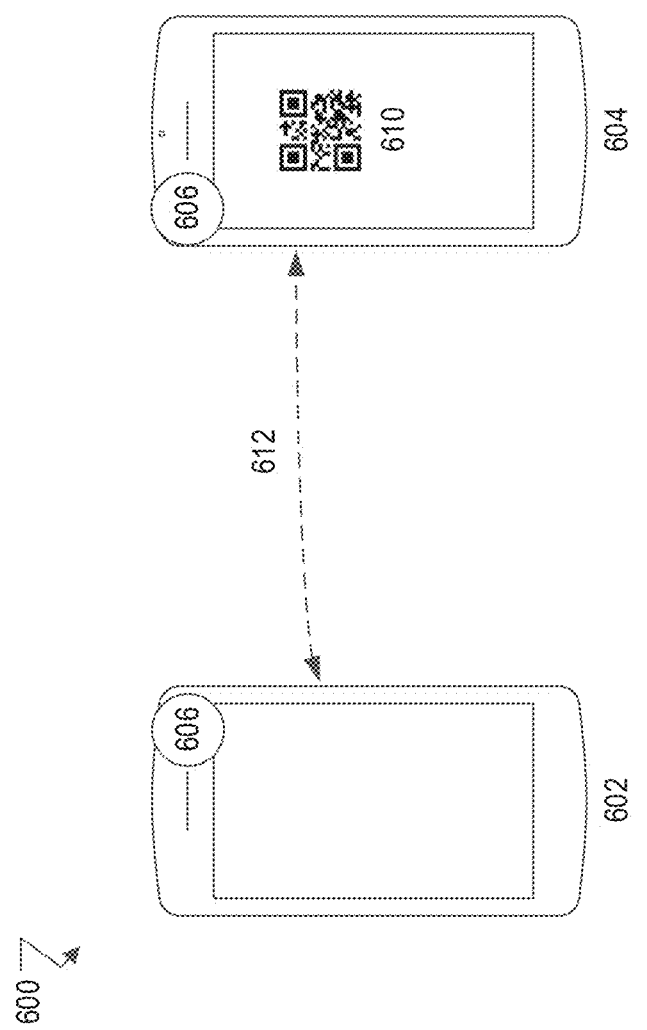
FIGS. 9-13 are diagrams of approaches to establishing a wireless communication channel.

FIG. 9 shows an image recognition approach 600 to establishing a wireless communication channel between a first device (in this example, a first mobile device 602) and a second device (in this example, a second mobile device 604). In an image recognition approach, a connection is requested by positioning the first mobile device 602 in the field of view of an optical sensor (e.g., a camera 606) of the second mobile device 604. The camera 606 acquires or otherwise senses an image of all or a portion of the first mobile device 602. The image is analyzed by a processor in the second mobile device 604 or by a remote processor accessible to the second mobile device 604 through an Internet or cellular connection to determine an identifier of the first mobile device 602. For instance, the camera 606 can acquire an image of a symbol 610, such as a quick response (QR) code, on the first mobile device 602. The symbol is representative of an identifier of the first mobile device 602. A wireless communication channel 612 is established between the first mobile device 602 and the second mobile device 604, or the first mobile device 602 is enabled to access an existing wireless communication channel to which the second mobile device 604 belongs.

In some examples, the first mobile device can be authenticated based on the analyzed image. For instance, a mobile device 602 having a symbol 610 previously registered with an administration system can be authenticated. The registration of symbols 610 can provide an added level of security, preventing devices not previously registered from joining a wireless communication channel with the second mobile device 604. Registered symbols can be stored in a data storage, such as a database, local to the second mobile device 604 or in a remote location accessible to the second mobile device 604 through an Internet or cellular connection.

Figure 10:
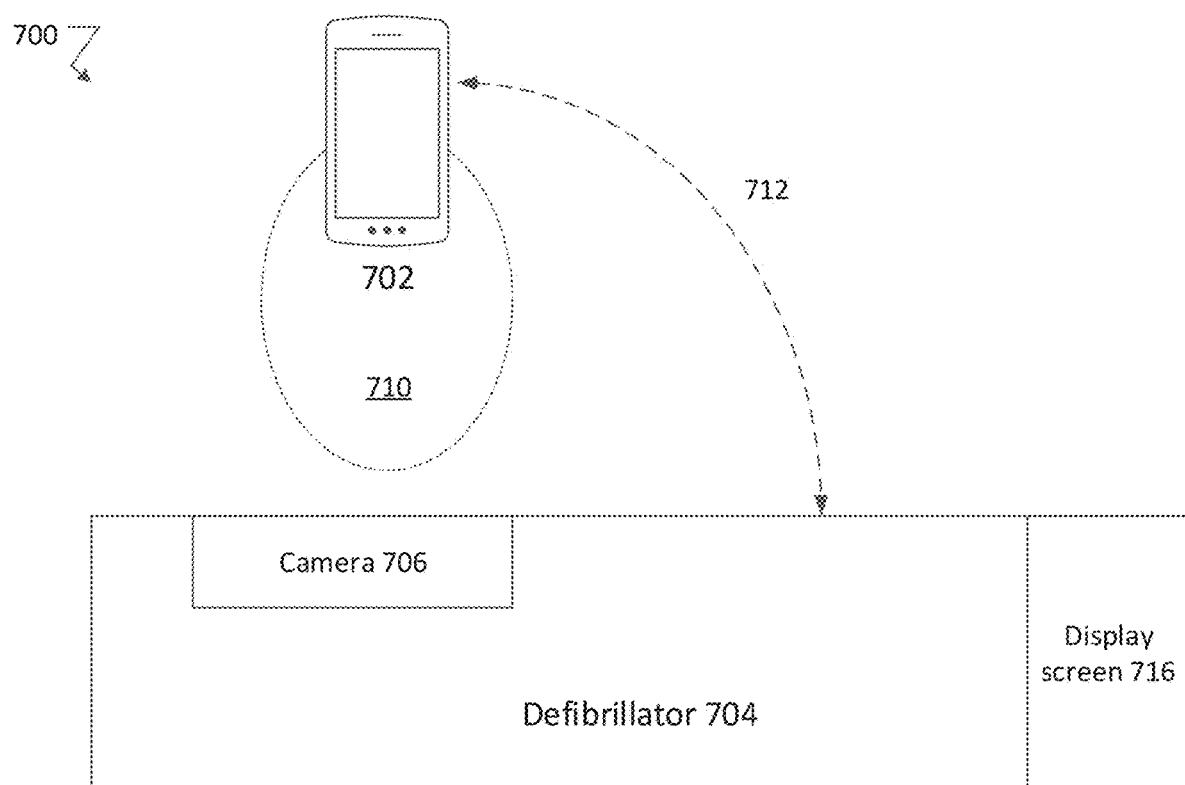

FIG. 10 shows a gestural recognition approach 700 to establishing a wireless communication channel between a first device (in this example, a mobile device 702) and a second device (in this example, a defibrillator 704). In a gestural recognition approach, the mobile device 702 is positioned in the field of view of an optical sensor (e.g., a camera 706) of the defibrillator 704 and moved in a specific pattern 710, e.g., in the shape of a circle, an "X," a cross, or another pattern. The pattern 710 is representative of an identifier of the mobile device 702. The camera 706 acquires or senses data indicative of the movement of the mobile device 702, such as a video or a vector representation of the movement. The pattern of movement is analyzed by a processor in the defibrillator 704 or by a remote processor accessible to the defibrillator 704 through an Internet or cellular connection to determine the identifier of the mobile device 702. A wireless communication channel 712 is established between the mobile device 702 and the defibrillator 704, or the mobile device 702 is enabled to access an existing wireless communication channel to which the defibrillator 704 belongs.

In some examples, the defibrillator 704 includes a display screen 716. The view of the camera 706 or a tracking of the pattern 710 of motion can be displayed on the display screen 716, e.g., to provide feedback to a user of the mobile device 702. For instance, the user can view the tracking of the pattern 710 to determine whether he or she made the intended pattern 710.

In some examples, the mobile device 702 can be authenticated based on the analyzed image. For instance, if the pattern of movement or the vector representation of the movement is recognized as a previously registered pattern of movement, the first mobile device is authenticated. The registration of patterns of movement can provide an added level of security, preventing devices not previously registered from joining a wireless communication channel with the defibrillator 704. Registered patterns of movement can be stored in a data storage, such as a database, local to the defibrillator 704 or in a remote location accessible to the defibrillator 704 through an Internet or cellular connection.

Figure 11:
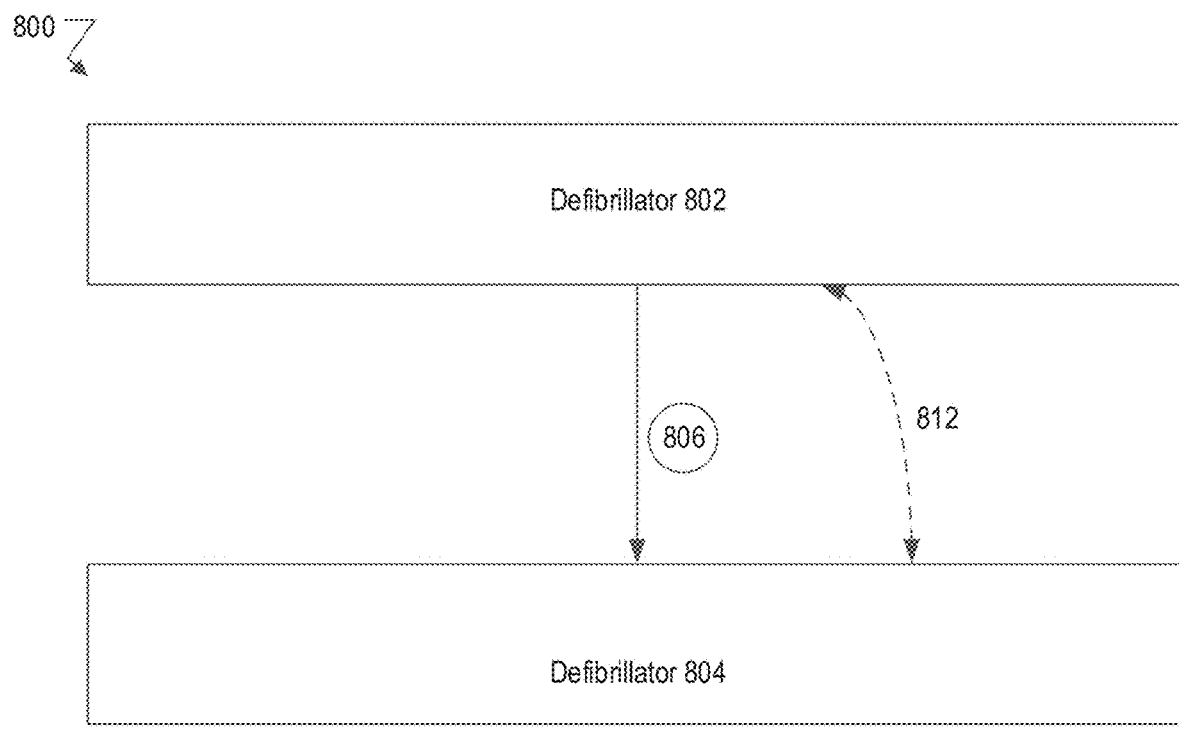

FIG. 11 shows a signal transmission approach 800 to establishing a wireless communication channel between a first device (in this example, a first defibrillator 802) and a second device (in this example, a second defibrillator 804). In a signal transmission approach, the first defibrillator 802 requests to enter into a wireless communication channel with the second defibrillator 804 by sending a signal 806 to the second defibrillator 804. The signal 806 is transmitted via a close proximity communication protocol, such as NFC, RFID, Bluetooth, or another communication protocol. The signal 806 can include an identifier of the first defibrillator 802. Responsive to receipt of the signal 806, a wireless communication channel 812 is established between the defibrillator 802 and the defibrillator 804, or the defibrillator 802 is enabled to access an existing wireless communication channel to which the defibrillator 804 belongs.

In some examples, for added security, the signal 806 can include data encrypted using an encryption key. The second defibrillator 804 can use the encryption key to decrypt an encrypted data element, such as a security code for enabling the wireless communication channel 812. If the security code can be successfully decrypted using the encryption key, the first defibrillator 802 is authenticated. The transmission of data encrypted with an encryption key prevents devices not previously registered from joining a wireless communication channel 812 with the second defibrillator 804. In some examples, the devices (e.g., the first defibrillator 802 and the second defibrillator 804) store predetermined encryption keys, e.g., one or more encryption keys common to the devices. In some examples, the encryption keys are exchanged among the devices using a key exchange technique such as the Diffie-Hellman protocol. In some examples, a public key technique is used, in which each device stores a private key (e.g., private to that device) that is not shared with other devices, and further the devices are configured to transmit public keys among each other. Data encrypted using a public key technique can include a secret encryption key (sometimes referred to as a symmetric key) shared between two (or more) of the devices.

Figure 12:
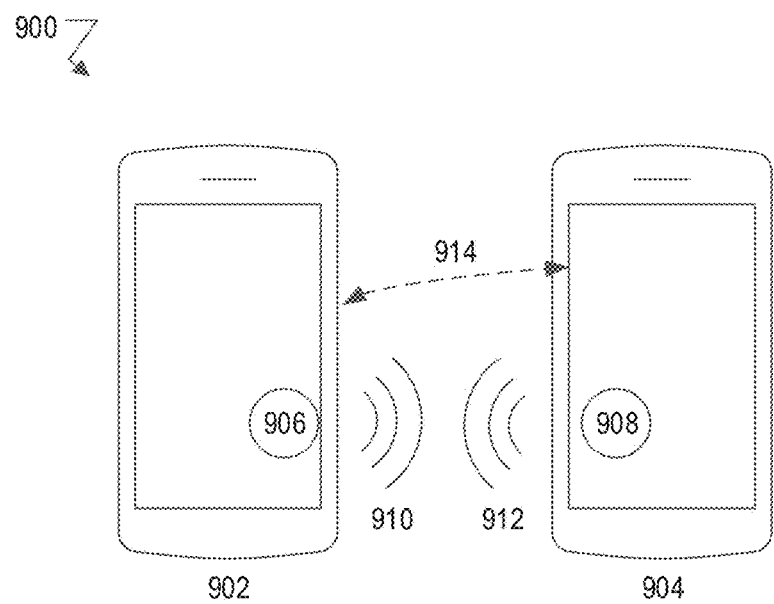

FIG. 12 shows a non-contact approach 900 to establishing a wireless communication channel between a first device (in this example, a first mobile device 902) and a second device (in this example, a second mobile device 904). In a non-contact approach 900, the first and second mobile devices 902, 904 each includes an electric field sensor 906, 908 that can detect when an electric field is impinging on an electric field generated by the sensor 906, 908. For instance, the sensors 906, 908 can each be an indium tin oxide (ITO)-based device capable of generating a local electric field 910, 912, respectively, e.g., an electric field that penetrates about ⅛ inch or 1/16 inch away from the sensor 906, 908. When the first mobile device 902 approaches the second mobile device 908, the local electric field 910 generated by the sensor 906 in the first mobile device 902 impinges on the local electric field 912 generated by the sensor 908 in the second mobile device 904. The impinging of the electric field 910 on the electric field 912 causes a perturbation in both electric fields 910, 912. The detection of this perturbation acts as a request for connection by the first mobile device 902. Responsive to detecting the perturbation, a wireless communication channel 914 is established between the first and second mobile devices 902, 904, or the first mobile device 902 is enabled to access an existing wireless communication channel to which the second mobile device 904 belongs.

Figure 13:
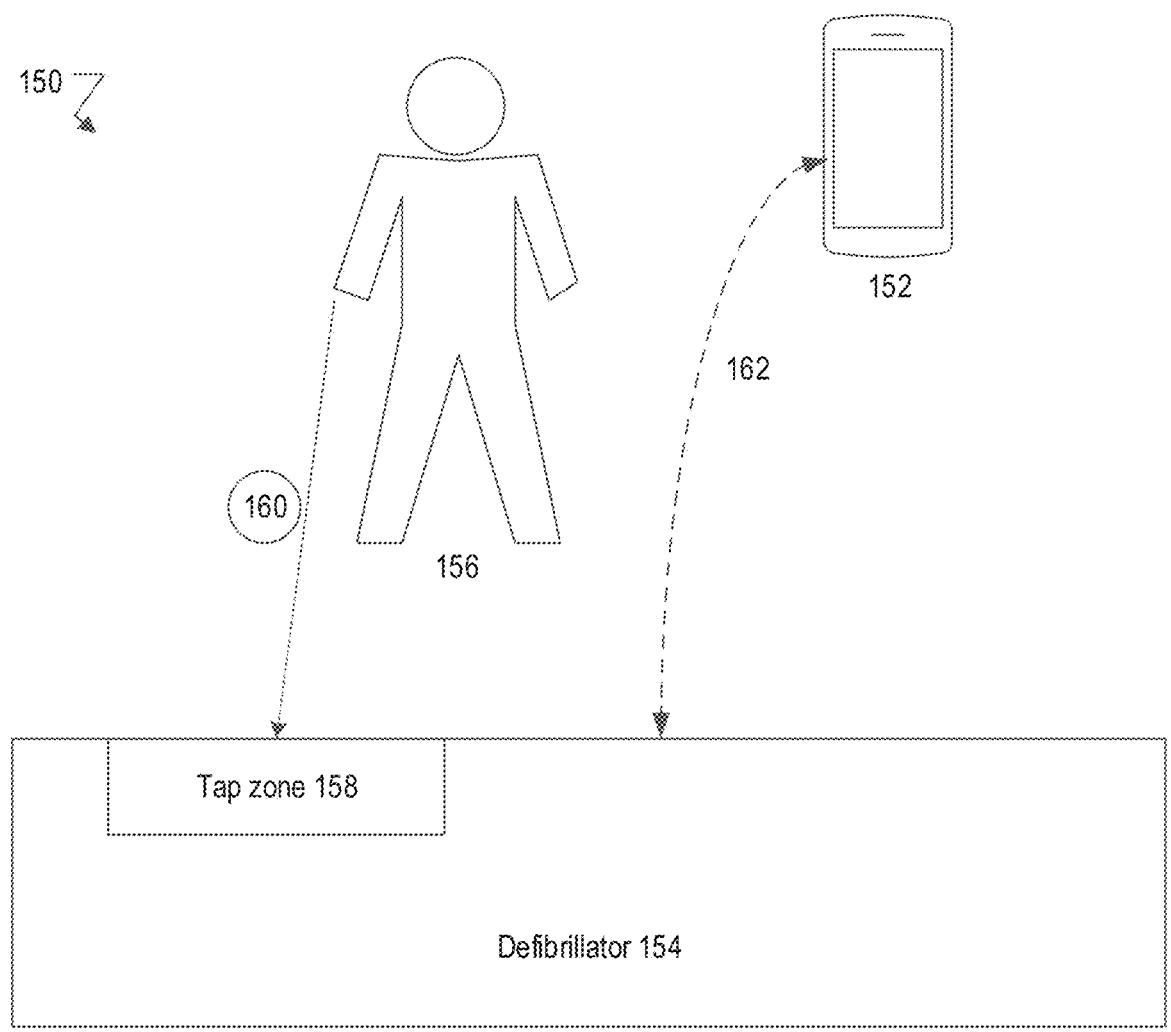

FIG. 13 shows a body network approach 150 to establishing a wireless communication channel between a first device (in this example, a mobile device 152) and a second device (in this example, a defibrillator 154). In a body network approach, a person 156 in contact with the mobile device 152 touches a tap zone 158 on the defibrillator 154. The person 156 can be, e.g., a rescuer wearing the mobile device 152 as a watch, a patient having the mobile device 152 resting on his chest, or another person. The tap zone 158 on the defibrillator detects the person's touch and receives a signal 160 including an identifier of the mobile device 152 that is transmitted through the person's body in a human body communication process, e.g., as described in U.S. patent application Ser. No. 14/036,501, entitled "Localized Monitoring," filed Sep. 25, 2013, the entire contents of which are incorporated here by reference. Responsive to receipt of the signal 160, a wireless communication channel 162 is established between the mobile device 152 and the defibrillator 154, or the mobile device 152 is enabled to access an existing wireless communication channel to which the defibrillator 154 belongs.

In some examples, combinations of the approaches described above can act as a request for connection. For instance, the detection of an object tapping on the tap zone of a device (e.g., a defibrillator or a mobile device) can cause a camera in the device to be activated. The camera can then detect the identifier of the object via image recognition or gestural recognition.

In some examples, a device (e.g., a defibrillator or mobile device) can include a light sensor, such as a 1-pixel camera, that can detect the presence of an object in the field of view of the light sensor. The detection of an object can cause a larger camera in the device to be activated. The camera can then detect the identifier of the object via image recognition or gestural recognition.

Figure 14:
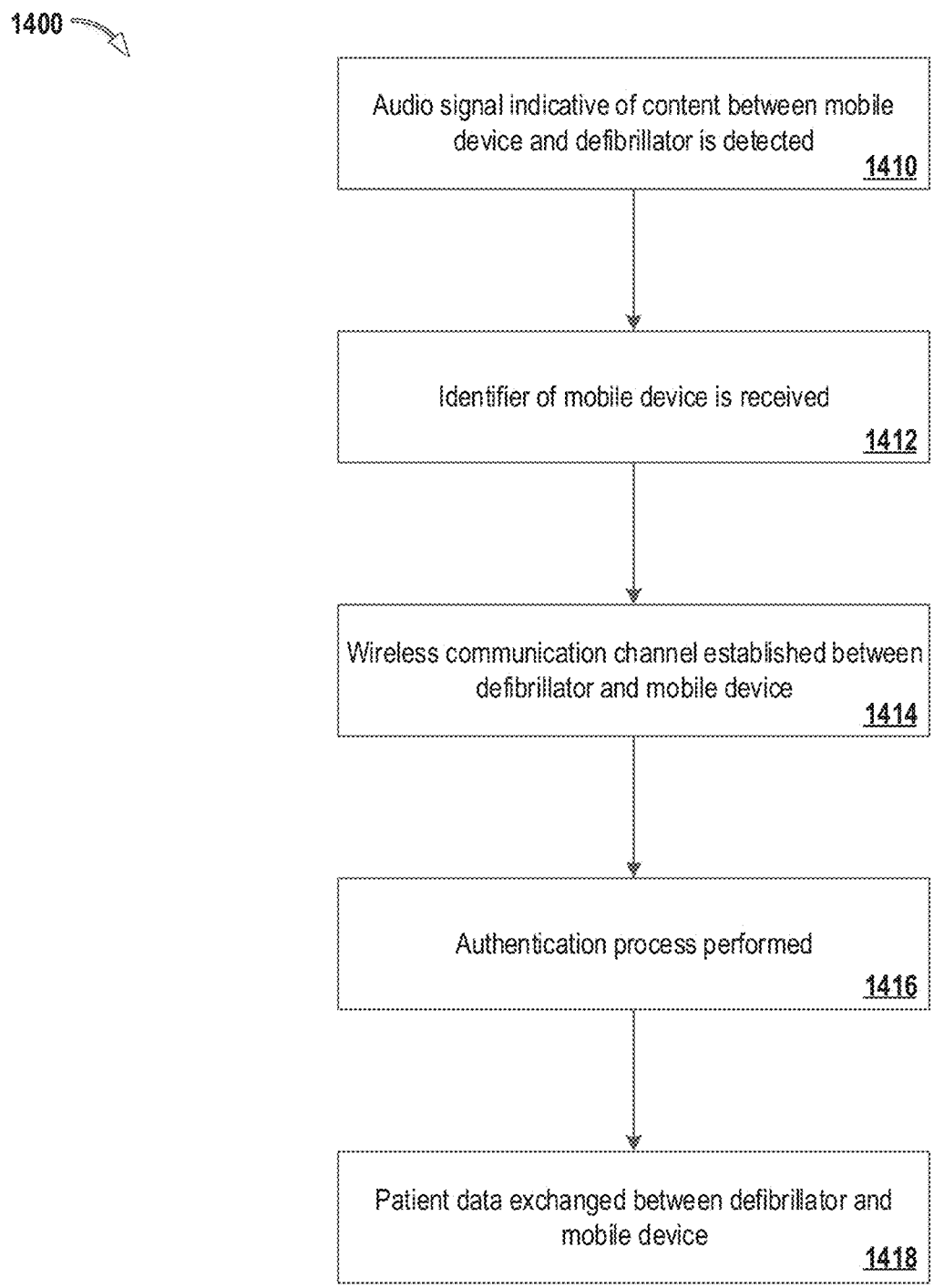
FIG. 14 is a flow chart.

Referring to FIG. 14, in a specific approach to establishing a wireless communication channel, a defibrillator detects an audio signal or another signal (e.g., accelerometer signal, force signal, image, etc.) indicative of contact between a mobile device and the defibrillator (10), e.g., indicative of the mobile device tapping against the tap zone of the defibrillator. The defibrillator receives an identifier of the mobile device through a close proximity communication protocol, such as NFC, RFID, or Bluetooth, between the defibrillator and the mobile device (12). The defibrillator enables a secure wireless communication channel to be established between the defibrillator and the mobile device based on the identifier of the mobile device and an identifier of the defibrillator (14). The defibrillator performs an authentication process (16) to determine that the audio or other signal was detected substantially concurrently with an acceleration of the mobile device. Once the wireless communication is established, patient data can be exchanged between the defibrillator and the mobile device (18). The patient data can include treatment data indicative of treatment provided to the patient using one or more of the mobile device and the defibrillator. The patient data can include health data indicative of a health status of the patient.

In some examples, a first device can request to disconnect from the wireless communication channel via a proximity-based interaction with a second device that belongs to the wireless communication channel. The request for disconnection can be the same type of interaction and/or sensed feature as that which acts as a request for connection. For instance, both the request for connection and the request for disconnection can be a tap zone interaction in which the first device is tapped against the second device. The request for connection and the request for disconnection can be the same interaction (e.g., a single tap), or the request for connection and the request for disconnection can be different interactions of the same type (e.g., a double tap to request a connection and a single tap to request disconnection). The request for disconnection and the request for disconnection can be different types of interactions. For instance, the request for connection can be by a signal transmission approach and the request for disconnection can be by a gestural recognition approach.

The ability for a device to request disconnection from the wireless communication channel can be useful, e.g., if the device is to remain at an emergency care scene but in a different role. For instance, at the scene of a mass casualty or mass rescue event, a rescuer may connect his mobile device to a first wireless communication channel while treating a first patient, but later disconnect from the first wireless communication channel in order to treat a second patient at the same scene. In some examples, when a mobile device has instantiated a first secure wireless communication with a first device and subsequently initiates a second secure wireless communication with a second device, the instantiation of the second secure wireless communication may automatically terminate the first secure wireless communication, without having to initiate a disconnect sequence.

Alternatively, if desired, rather than terminating the first secure wireless communication, a secure wireless communication channel may be established between all three devices. Hence, one device may act as a link in establishing secure wireless communications between separate devices. Once the spatial localization is determined, leading to authentication and establishment of a secure wireless channel between a first device and a second device, one of the devices, e.g., the first device, may undergo a similar process with a third device, which also establishes an authenticated and secure connection between the second device and the third device, eliminating the need for the process to be repeated a third time between the second and third devices.

The wireless communication channel can be configured as a mesh network or as a mesh network with a master node (sometimes referred to as a hub configuration). In a mesh network, a device can request connection from any of the nodes (devices) that form part of the network. In a hub configuration, a device can request connection only from a node (device) designated as a master node, but the network otherwise functions as a mesh network. A mesh network with a master node can have one or more master nodes.

In some examples, the configuration of the wireless communication channel can be determined based on the request for connection. For instance, a certain gesture or tap pattern (e.g., a single tap or a particular rhythm of tapping) can indicate that the request is for a mesh network and a different gesture or tap pattern (e.g., a double tap or a different rhythm of tapping) can indicate that the request is for a hub configuration. In some examples, the configuration can be based on the identifier of the device requesting connection or based on the authentication of the device requesting connection. For instance, if a device has a previously registered identifier or if a device is successfully authenticated, the wireless communication channel can be enabled in a mesh network configuration. If a device has an unregistered identifier or if a device cannot be authenticated, the wireless communication channel can be enabled in a hub configuration for additional security.

In some examples, user input can configure the wireless communication channel. For instance, an operator of a defibrillator can select whether to configure the wireless communication channel as a mesh network or a hub configuration.

In some examples, the wireless communication channel between devices can be established according to one or more rules, such as rules indicative of the duration for which the wireless communication channel is to be enabled. The rules can be based on the identifier of the device requesting connection or based on the authentication of the device requesting connection. For instance, if a device has a previously registered identifier or if a device is successfully authenticated, the wireless communication channel can be enabled for an unlimited duration. If a device has an unregistered identifier or if a device cannot be authenticated, the wireless communication channel can be enabled for a limited period of time for additional security. The rules can be specified by user input.

Other implementations are also within the scope of the following claims.

What is claimed is:

1. A system for establishing secure dynamically reconfigurable wireless communications between a patient monitor and a computing device, the system comprising:
the patient monitor comprising one or more physiological sensors configured to measure physiological data from a patient and the patient monitor being configured to perform a close proximity wireless communication protocol;
the computing device comprising a receiver and a transmitter configured to establish a secure communication channel with the patient monitor according to the close proximity wireless communication protocol, the secure communication channel having an effective range of less than 100 cm to the patient monitor;
a sensor configured to detect at least one feature from an immediate environment of the patient monitor; and
a processor and a non-transitory computer readable storage medium encoded with a computer program comprising instructions that, when executed, cause the processor to perform operations comprising:
detecting a request for connection between the patient monitor and the computing device based at least in part on the at least one feature of the immediate environment,
determining whether spatial localization is achieved between the patient monitor and the computing device based at least in part on the at least one feature of the immediate environment,
initiating a mutual authentication between the computing device and the patient monitor based at least in part on the spatial localization, and
establishing the secure communication channel between the patient monitor and the computing device for exchanging patient data.

2. The system of claim 1, wherein the patient data comprises one or more of (i) treatment data comprising ECG signals of the patient, or (ii) patient information.

3. The system of claim 1, wherein the close proximity wireless communication protocol comprising at least one of Bluetooth Low Energy, Near Field Communication and ZigBee.

4. The system of claim 1, wherein the effective range of the secure communication channel with the patient monitor is greater than 20 cm.

5. The system of claim 4, comprising a second receiver and transmitter configured to establish an intermediate secure communication channel having a second range greater than 100 cm.

6. The system of claim 5, wherein the second receiver and transmitter are configured to maintain the secure communication channel between the patient monitor and the computing device.

7. The system of claim 5, wherein the intermediate secure communication channel employs a protocol comprising at least one of Bluetooth, Wi-Fi, ISM radio band, and ZigBee.

8. The system of claim 1, wherein determination of whether the spatial localization is achieved is based on whether a threshold is met by the at least one feature.

9. The system of claim 8, wherein the threshold comprises at least one of a detected distance, a sound signal, acceleration, velocity, pressure or power level.

10. The system of claim 1, wherein the secure communication channel is established based on a correlation between the at least one feature detected by the patient monitor and the computing device.

11. The system of claim 1, wherein the secure communication channel uses an encryption and proximate tokens between the patient monitor and the computing device, wherein the proximate tokens or the at least one feature for determining spatial localization is mutually known by the patient monitor and the computing device without requiring transmission to the other device, and wherein the proximate tokens are used in a secure key-exchange protocol.

12. The system of claim 11, wherein the proximate tokens comprise random values input into the secure key-exchange protocol.

13. The system of claim 11, wherein the proximate tokens are based on an occurrence of an event related to the at least one feature.

14. The system of claim 13, wherein the event comprises at least one of a time of the occurrence, an elapsed time from the occurrence, a contact pressure, a time of release from contact, a velocity of release from contact, a velocity of detected motion, a shape of a path of a gestural motion, a velocity of movement of an object in an image.

15. The system of claim 1, wherein the receiver is the sensor.

16. The system of claim 15, wherein the sensor is configured to measure a field strength of electromagnetic energy for estimating a degree of proximity between the patient monitor and the computing device.

17. The system of claim 1, wherein the sensor comprises at least one of a camera, a motion sensor and an acoustic sensor.

18. The system of claim 1, wherein the at least one feature of the immediate environment measured by the sensor comprises at least one of an image, a sound, a movement, a code, gestural motion, contact between the patient monitor and the computing device, acceleration and velocity.

19. The system of claim 1, wherein the at least one feature comprises a plurality of features and the spatial localization is based on a correlation between the plurality of features.

20. The system of claim 19, wherein the sensor comprises two or more of a motion sensor, a pressure sensor, a visual sensor, and an acoustic sensor and the correlation is performed between at least one of: a motion measured by the motion sensor and a pressure measured by a the pressure sensor, a motion measured by the motion sensor and a sound measured by the acoustic sensor, a motion measured by the motion sensor and a motion measured by a second motion sensor, a pressure measured by the pressure sensor and a sound measured by the acoustic sensor, a visual image measured by the visual sensor and a motion measured by the motion sensor, a visual image measured by the visual sensor and a display provided by the patient monitor, or a sound measured by the acoustic sensor and a sound measured by a second acoustic sensor.

21. The system of claim 1, wherein the processor is configured to detect a request for disconnection based on the at least one feature.

22. The system of claim 1, wherein the processor is configured to detect a request for disconnection based on a second feature detected by the patient monitor or the computing device.

23. The system of claim 1, wherein the patient data comprises one or more of data indicative of a shock delivered to the patient, a rate of chest compressions delivered to the patient, a depth of chest compressions delivered to the patient, a duration of compressions delivered to the patient, medication administered to the patient, a rate of ventilation flow to the patient, and a volume of ventilation flow to the patient.

24. The system of claim 1, wherein the physiological data comprises one or more of an electrocardiogram (ECG) signal of the patient, a blood pressure of the patient, end tidal carbon dioxide of the patient, pulse oximetry of the patient, a temperature of the patient, a respiration rate of the patient, a blood oxygen level of the patient, a pulmonary function of the patient, and a blood glucose level of the patient.

25. The system of claim 1, wherein the at least one feature from the immediate environment of the patient monitor comprises at least one of environmental information, ambient temperature, patient location, air pressure, motion information, and audio information.

26. The system of claim 1, wherein the computing device is a mobile computing device.

27. The system of claim 1, wherein the patient monitor comprises at least one of a defibrillator, a ventilator, a wearable defibrillator, and a wearable monitor.

28. The system of claim 1, wherein the patient monitor comprises an accelerometer configured to measure compression parameters comprising one or more of a rate, a depth and a duration of chest compressions.

29. The system of claim 1, wherein the processor performs the operations comprising:
in response to exchanging the patient data, coordinating chest compression prompting with defibrillation.

30. The system of claim 1, wherein the mutual authentication comprises:
exchanging secure identifiers between the patient monitor and the computing device based at least in part on the spatial localization.

31. The system of claim 1, wherein the processor performs the operations comprising:
determining that spatial localization is achieved between the patient monitor and the computing device to provide mutual authentication, and
in response to determining that the spatial localization is achieved, establishing the secure communication channel between the patient monitor and the computing device.

32. The system of claim 1, wherein the mutual authentication is based at least in part on a temporal localization between the patient monitor and the computing device relative to one another.

33. The system of claim 1, wherein the mutual authentication is based at least in part on matching a parameter of an event related to the at least one feature with a pre-agreed-to parameter.

34. The system of claim 1, wherein the mutual authentication occurs prior to establishment of the secure communication channel.

* * * * *

UNITED STATES PATENT AND TRADEMARK OFFICE
CERTIFICATE OF CORRECTION

PATENT NO. : 10,888,229 B2
APPLICATION NO. : 16/685613
DATED : January 12, 2021
INVENTOR(S) : Gary A. Freeman et al.

Page 1 of 1

It is certified that error appears in the above-identified patent and that said Letters Patent is hereby corrected as shown below:

In the Claims

Column 42, Line 45, Claim 20, delete "by a" insert -- by --

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*